United States Patent
Novak et al.

[11] Patent Number: 5,561,412
[45] Date of Patent: Oct. 1, 1996

[54] PATIENT/NURSE CALL SYSTEM

[75] Inventors: Joseph H. Novak, Batesville; Julie E. Myers, Indianapolis; Curt E. Geiger, Oldenburg, all of Ind.; Daniel J. Ulrich, Cincinnati, Ohio; Robert J. Jennings, Annandale, Va.; Matthew W. Weismiller, Batesville, Ind.; Philip D. Palermo, Sidney, Ohio

[73] Assignee: Hill-Rom, Inc., Batesville, Ind.

[21] Appl. No.: 90,804

[22] Filed: Jul. 12, 1993

[51] Int. Cl.$^6$ .................................................. H04Q 1/00
[52] U.S. Cl. ............................... 340/286.07; 340/286.06; 340/825.08; 340/825.52
[58] Field of Search ........................... 340/286.07, 573, 340/825.52, 825.08, 332, 323 R, 286.01, 286.06, 286.08, 286.09, 825.36, 825.49; 364/413.02, 413.03; 379/38

[56] References Cited

U.S. PATENT DOCUMENTS

| | | | |
|---|---|---|---|
| 2,330,356 | 9/1943 | Belliveau | 340/825.49 |
| 2,335,524 | 11/1943 | Lomax | 340/825.49 |
| 2,736,888 | 2/1956 | McLain | 340/316 |
| 2,896,021 | 7/1959 | Philipps | 379/38 |
| 3,098,220 | 7/1963 | De Graaf | 340/825.48 |
| 3,439,320 | 4/1969 | Ward | 367/191 |
| 3,478,344 | 11/1969 | Schwitzgebel et al. | 340/825.44 |
| 3,553,383 | 1/1971 | Rochtus | 379/217 |
| 3,599,200 | 8/1971 | Bunting | 340/286.07 |
| 3,696,384 | 10/1972 | Lester | 367/199 |
| 3,739,329 | 6/1973 | Lester | 367/6 |
| 3,767,859 | 10/1973 | Doering | 379/106 |
| 3,805,265 | 6/1974 | Lester | 342/44 |
| 3,973,200 | 8/1976 | Akerberg | 340/825.44 |
| 4,067,005 | 1/1978 | Levy et al. | 340/573 |
| 4,150,284 | 4/1979 | Trenkler et al. | 359/158 |
| 4,151,407 | 4/1979 | McBride | 359/158 |
| 4,216,462 | 8/1980 | McGrath et al. | 364/413.03 |
| 4,225,953 | 9/1980 | Simon et al. | 367/117 |
| 4,228,426 | 10/1980 | Roberts | 340/573 |
| 4,237,344 | 12/1980 | Moore | 379/38 |
| 4,264,982 | 4/1981 | Sakarya | 359/146 |
| 4,275,385 | 6/1981 | White | 340/825.49 |

(List continued on next page.)

FOREIGN PATENT DOCUMENTS

| | | |
|---|---|---|
| 2211765 | 7/1974 | France . |
| 1287190 | 1/1969 | Germany . |

OTHER PUBLICATIONS

"The Active Badge Location System" ACM Transactions on Information Systems, vol. 10, No. 1, Jan. 1992, pp. 91–102.
"Big Brother, Pinned to Your Chest", Business Week, Aug. 17, 1992.
"'Active Badges' Play Follow the Worker", The Washington Post Oct. 8, 1992, p. A1, continued on A18.

*Primary Examiner*—John K. Peng
*Assistant Examiner*—Edward Lefkowitz
*Attorney, Agent, or Firm*—Wood, Herron & Evans, P.L.L.

[57] ABSTRACT

A patient/nurse call system for a hospital includes patient stations capable of generating hospital calls and a remote master station which prioritizes and stores the calls. Hall units outside patient rooms identify the rooms from which the calls originate and the type of call. Each patient station allows selective retrieval and display of unanswered calls, and the system further permits audio interconnection between any two of the stations. Nurse-worn badges transmit pulse-coded infrared signals which are received by receivers at the patient stations and in response, the system generates identity and location signals which are stored at the master station. The nurse location and identity information may also be retrieved and displayed at any patient station. Receipt of a nurse's infrared signal at a room station automatically cancels a patient call originating from the room and display thereof by the respective hall unit, while actuating a display to indicate nurse presence. Bed monitoring units also interconnect to the patient stations to generate signals related to bed status.

35 Claims, 9 Drawing Sheets

Microfiche Appendix Included
(2 Microfiche, 126 Pages)

U.S. PATENT DOCUMENTS

| | | | |
|---|---|---|---|
| 4,298,863 | 11/1981 | Natitus et al. | 340/573 |
| 4,331,953 | 5/1982 | Blevins et al. | 340/539 |
| 4,356,475 | 10/1982 | Neumann et al. | 340/870.13 |
| 4,418,334 | 11/1983 | Burnett | 340/332 |
| 4,455,548 | 6/1984 | Burnett | 340/293 |
| 4,539,560 | 9/1985 | Fleck et al. | 340/573 |
| 4,577,185 | 3/1986 | Anderson | 340/573 |
| 4,578,671 | 3/1986 | Flowers | 340/636 |
| 4,598,275 | 7/1986 | Ross et al. | 340/573 |
| 4,601,064 | 7/1986 | Shipley | 359/172 |
| 4,649,385 | 3/1987 | Aires et al. | 379/57 |
| 4,680,790 | 7/1987 | Packard et al. | 340/286.07 |
| 4,709,330 | 11/1987 | Yokoi et al. | 364/400 |
| 4,740,788 | 4/1988 | Konneker | 340/825.44 |
| 4,752,951 | 6/1988 | Konneker | 379/211 |
| 4,792,798 | 12/1988 | Wilowski | 340/286.07 |
| 4,795,905 | 1/1989 | Zierhut | 250/338.1 |
| 4,833,467 | 5/1989 | Kobayashi et al. | 340/825.64 |
| 4,837,568 | 6/1989 | Snaper | 340/825.54 |
| 4,947,152 | 8/1990 | Hodges | 340/286.07 |
| 4,955,000 | 9/1990 | Nastrom | 367/117 |
| 4,967,195 | 10/1990 | Shipley | 340/286.07 |
| 4,990,892 | 2/1991 | Guest et al. | 340/573 |
| 4,998,095 | 3/1991 | Shields | 340/574 |
| 5,027,314 | 6/1991 | Linwood et al. | 364/460 |
| 5,062,151 | 10/1991 | Shipley | 359/154 |
| 5,065,154 | 11/1991 | Kaiser et al. | 340/286.07 |
| 5,103,108 | 4/1992 | Crimmins | 250/338.1 |
| 5,124,991 | 6/1992 | Allen | 371/32 |
| 5,137,033 | 8/1992 | Norton | 128/886 |
| 5,153,584 | 10/1992 | Engira | 340/870.18 |
| 5,291,399 | 3/1994 | Chaco | 364/413.02 |
| 5,416,695 | 5/1995 | Stutman et al. | 364/413.02 |

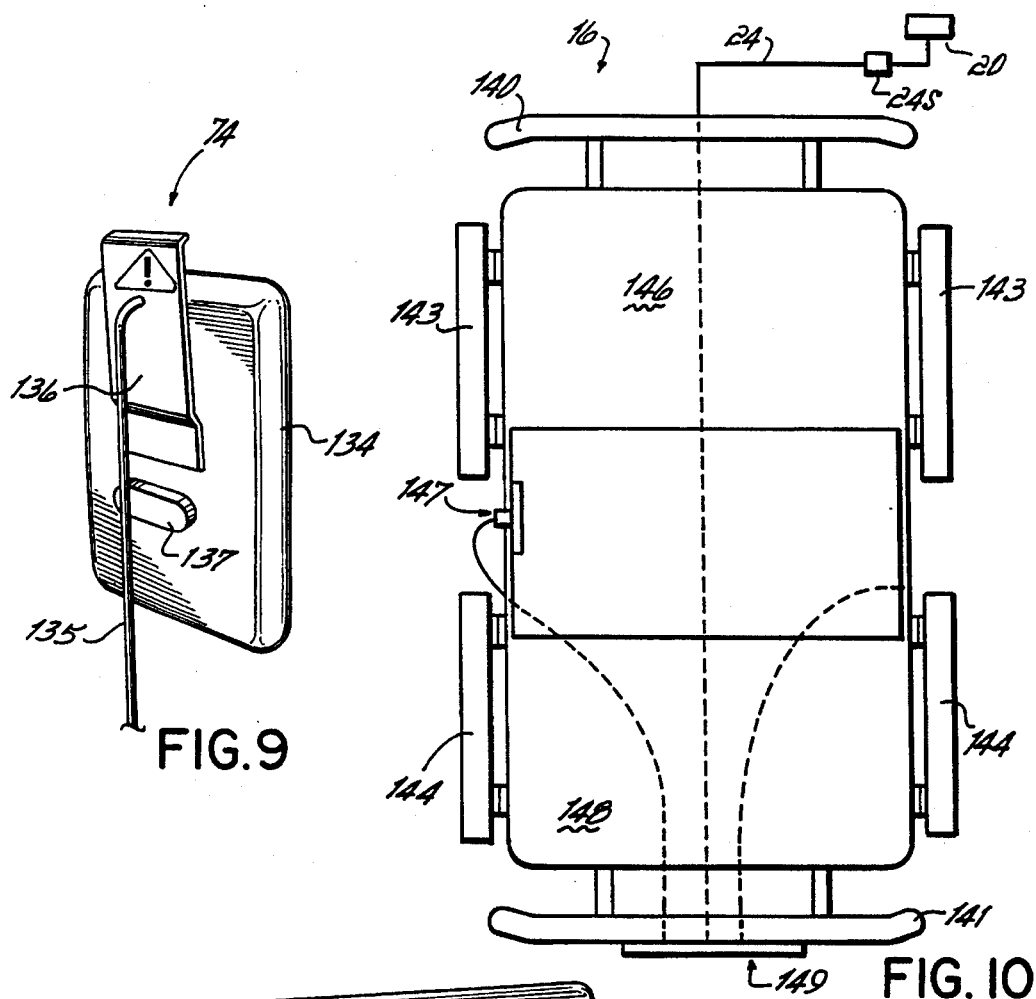
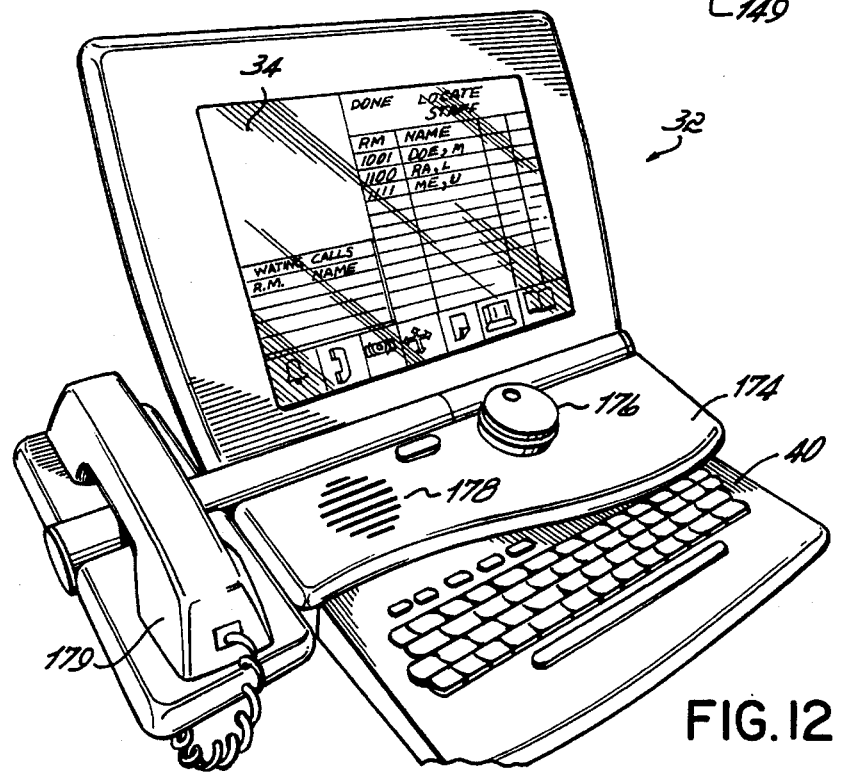

PATIENT/NURSE CALL SYSTEM

This application includes a microfiche appendix comprising 2 microfiche that include 126 frames.

FIELD OF THE INVENTION

This invention relates to a hospital communication system, and more particularly, to a user friendly patient/nurse call system with enhanced operational capability.

BACKGROUND OF THE INVENTION

Nurses and other staff in a hospital ward or hospital wing must work under varying conditions, which include high pressure, stress and long hours. These caregivers must remain alert to respond to patient needs, in emergency and nonemergency situations. Due to economic practicalities and the ever-increasing costs of medical care, it is necessary to make the most efficient use of nurses and staff on call in a hospital wing, particularly at night when nurse and staff levels are maintained at a minimum.

On the other hand, a desire to optimize the efficiency of nurse and staff personnel is of secondary importance relative to the primary objective, that of providing a high level of medical care. If nurse and staff levels are reduced for the sake of efficiency without any corresponding simplification of duties and responsibilities, the level of patient care will decrease.

It is one primary objective of this invention to maximize the efficiency of nurses and staff on call in a hospital wing, but to do so in a manner which does not increase the work load or stress levels of these professional caregivers.

One approach to maximizing the efficiency of nurses and other hospital staff involves the use of a location and identification system to continuously monitor the locations of these persons. For instance, White U.S. Pat. No. 4,275,385 discloses a personnel locating system where individuals to be located wear infrared transmitters, and each transmitter transmits a pulse-coded signal which corresponds to the identity of the wearer. This information is relayed and displayed at a central control unit. This information may also be displayed at remote terminals, used to lock restricted-access equipment or locations, or conveyed via a telephone interface to a telephone switching network to call the nearest telephone or to page the transmitter wearers.

Thus, to contact the transmitter-wearers, White requires that the location system interconnect with the telephone system and/or a paging system. This required interaction with another communication system increases the cost and complexity of interacting with the located personnel, due to the need for interfacing components. It also requires that personnel to be located either wear a receiving device, such as a pager, or that they be near a telephone.

A number of other U.S. Patents also disclose personnel locating or monitoring systems which purport to improve upon the system disclosed in the White patent. However, these improvements relate to the mechanics of signal detection, or the organization, maintenance and retrieval of stored information for making reports. These patents do not disclose use of a location system in a manner which helps nurses and staff do their jobs more efficiently and more effectively.

It is another objective of this invention to improve the overall effectiveness of a hospital personnel locating system so that the system directly benefits nurses and staff by increasing efficiency and effectiveness.

Almost every hospital wing or ward has a patient/nurse call system which includes an audio network to allow a patient in a hospital room to contact and speak with a nurse or staff member at a nurse station. Typically, the patient may activate a "call" signal by depressing a button on a small housing connected via hardwire to a unit mounted to the headwall of the patient room. This small housing is generally referred to as a pillow speaker, or pillow unit. The headwall unit usually has another wall-mounted call button for easy operation by a nurse. Other input mechanisms may include emergency call buttons, code blue buttons, or bathroom call buttons.

Additionally, the audio network of these call systems may be used for audio monitoring of a hospital room from the nurse station during an extreme emergency, such as a code "blue" status.

Hospitals also include emergency signaling devices for notifying hospital personnel of other types of emergency conditions, such as smoke detectors or a fire alarm. Typically, these devices generate audio signals to convey audible alarms over a hospital intercom system, which may or may not to be interconnected with the patient room audio network.

Some hospitals use bed monitoring devices with bed sensors which indicate bed conditions, such as "brakes on", mattress firmness (for inflatable mattresses), or incontinence.

The duplicity of these call and information systems in a hospital complicates the organization, maintenance and effective dissemination of all of the useful information that is generated. If these systems cannot be operated in a simple, user-friendly manner, they can add to the stress level of nurses and staff. As a result, their jobs are made more difficult, rather than easier.

Additionally, use of multiple call and information systems in a hospital adds to the costs of health care, due to costs associated with purchase, installation and maintenance of the various components of these multiple systems, along with training personnel how to use the system.

It is another objective of this invention to expand the operational capability of a patient/nurse call system.

It is still another objective of the invention to simplify interaction with and information retrieval from a hospital communication system, thereby to reduce stress levels of nurses and staff.

It is still another objective of this invention to eliminate duplicity in communication systems used within a hospital, thereby to reduce the costs of purchase, installation and maintenance of the components of multiple systems, along with reducing the costs associated with training hospital staff in the use of multiple systems.

It is still another objective of this invention to assist nurses and staff in achieving optimum efficiency in a hospital wing.

The above-stated objectives are achieved with an improved patient/nurse call system which generates and prioritizes all types of hospital calls and facilities answering of these calls from any one of a plurality of nurse stations or patient room stations in a hospital wing. The system has the capability of visually displaying all calls at any station, including stations located in the patient rooms, thereby to facilitate the dissemination of call information and to expedite responding to the calls.

Each patient room station interconnects to a plurality of input devices for generating the different calls used in a typical hospital, such as SMOKE ALARM, CODE BLUE, STAFF EMERGENCY, etc. These calls include patient-generated, nurse-generated or automatically generated calls. Calls may also be generated at one or more of the nurse stations.

The calls are forwarded to a master station, which prioritizes the calls according to status and time received. Outside of each patient room, in the hall, a hall unit mounted above the doorway displays an indication that a call has originated from the room. The hall units connect directly to the patient room stations.

Each patient room station preferably has a display and selection controls to allow retrieval and display of all calls. Thus, after responding to a call in a first patient room, a nurse at that patient station can retrieve and display the remaining calls and then respond to the highest priority unanswered call.

The system also provides for audio interconnection between any two stations. This audio interconnection capability, along with the display of unanswered calls, facilities oral communication among nurse, hospital staff and patients, thereby promoting efficiency in responding to calls.

Preferably, the nurses on duty in the hospital wing wear nurse locator badges, and these badges transmit pulsed-coded infrared signals to receivers operatively connected to the patient stations. In response, the patient stations generate corresponding identification signals unique to the wearer of the badge. The system then couples each identification signal with a location signal to form a signal pair, with the identification signal corresponding to the patient station of receipt. The signal pairs are automatically downloaded and stored at the master station.

This nurse identification and location information may be displayed at the master station, or at any of the other stations. This allows a person at any station to visually display the identifications and locations of the nurses on duty in the wing, in addition to unanswered calls. This combination of display features optimizes the communication capabilities among nurses, hospital staff and patients in a hospital wing. Thus, rather than serving primarily as a nurse monitoring system, as in some prior nurse locating systems, this system facilitates communication among nurses and staff and optimizes information flow to nurses and staff in a simple, user-friendly manner, thereby increasing efficiency and effectiveness.

In conjunction with the nurse locator badges, the system also provides for automatic cancelling of a patient call, and automatic cancelling of the visual display of the call by the respective hall unit, after a nurse wearing a badge is sensed by the respective patient station. Receipt of a nurse signal does not cancel higher priority calls, such as CODE BLUE, BATHROOM call. Preferably, a visual indicator at each patient station indicates that a call has been received. The respective hall unit also visually displays nurse presence within the respective patient room.

In another mode, referred to as "nurse follower", a patient call generated from a patient room is automatically signalled audibly to the nurse assigned to that room, wherever the nurse is located. In short, the patient-placed call "follows" the nurse. This allows the nurse to immediately initiate an audio conversation with the patient to assess the importance of the call, without requiring the nurse to leave the room he or she is already in.

According to a preferred embodiment of the invention, an improved patient/nurse call system for a hospital wing includes a master station, a plurality of patient stations, (although referred to as "patient" stations, these stations may also be located in nurse or staff areas) and nurse-worn transmitter badges. A private branch exchange (PBX) system interconnects the master station and the other stations, and each room has an intra-room network. The intra-room network includes a hall unit mounted in the hall way and at least one patient station, at least one receiver, and inputs for generating digital signals related to calls or bed status information.

The master station provides communication capabilities for the other stations. It receives, stores and sends call information, instructions and status messages from the stations, and it controls and monitors all aspects of the system. The master station includes a console with a display, a control wheel and a handset. The master station further includes a personal computer with memory capacity for storing hospital calls and nurse location and identification information generated by the system.

Each patient station in a hospital room is associated with a single patient bed, although the system could also be configured so that each station would accommodate multiple beds. Each patient station includes a wall-mounted housing with a control wheel, a display, call generation/cancellation buttons, indicating lights and an audio speaker. Nurses at a patient station can readily retrieve stored, unanswered calls or nurse location information from the master station by operation of the user-friendly control wheel and display.

The private branch exchange operates as a voice/data switching system for establishing audio links and data distribution between the master station and the other stations. The master station interconnects with the PBX via an RS-232 serial data line, and the PBX interconnects with each patient station via a twisted pair telephone line. The network for the system is basically a telephone network which provides synchronous, full duplex, voice and data communications between any two patient stations or between any patient station and the master station. It also allows two way audio links or connections between multiple pairs of stations. The PBX is a transparent device from the standpoint of signal content and interaction. It simply provides an audio and data communications link between any two stations upon request.

Each interaction between a patient station and the PBX is actually routed through an input/output board dedicated to the patient room in which the station is located. This I/O board routes all signals to or from the patient room, including generation of calls by input devices, display of calls at the hall unit associated with each room, and generation of a nurse identification signal in response to receipt of a pulse-coded signal from a nurse-worn badge. The I/O board controls the network associated with that patient room, i.e. the intra-room network.

When a PATIENT call is generated at a station, the I/O board signals the hall unit to illuminate a display light designated for PATIENT calls. The call is also routed to the master station via the PBX, where it is categorized according to priority and then stored. Preferably, the master station continuously displays all received and stored calls, and these calls are routed for display at any of the patient stations upon request at the patient station.

Similarly, the nurse location and identify information can also be retrieved for display at each patient station via operation of the control wheel and the display.

This invention expands the operational capability of a patient/nurse call system to facilitate locating, prioritizing and responding to all types of hospital calls in a systematic way. Because of its simplicity in operation, this improved patient/nurse call system reduces the required amount of training time normally associated with learning a new communication system, in addition to reducing the stress level of nurses and staff on duty in a hospital wing.

This improved patient/nurse call system provides generation, storage, retrieval and display of hospital calls, generation, storage, retrieval and display of nurse identity and location information, automatic display and cancelling of calls, an audio interconnection between any two stations, and multiple two way audio interconnections between station pairs. As a result, this invention reduces the overall hospital costs associated with installing and maintaining multiple systems with duplicative and/or overlapping capabilities, thereby resulting in a cost savings to the hospital.

These and other features of the invention will be more readily understood in view of the following detailed description and the drawings.

BRIEF DESCRIPTION OF THE DRAWINGS

FIG. 9 is a perspective view of a bath station or a shower station for a patient/nurse call system in accordance with this invention.

FIG. 10 is a schematic plan view which depicts a patient hospital bed for a patient/nurse call system in accordance with this invention.

FIG. 12 is a perspective view of a master station for a patient/nurse call system in accordance with this invention.

DETAILED DESCRIPTION OF THE DRAWINGS

I. The Calls

Before describing the detailed structure and operation of the patient/nurse call system of this invention, a review of the following table will familiarize the reader with the types of calls handled by the system and assist in understanding the system. The table identifies the calls generated by the system and provides an indication of how these calls are generated.

TABLE 1

| CALLS | PRIORITY | GENERATED |
| --- | --- | --- |
| SMOKE ALARM | 1 | automatically/input device |
| CODE BLUE | 2 | human operator/input device |
| STAFF EMERGENCY | 3 | human operator/input device |
| BATHROOM | 4 | human operator/input device |
| SHOWER | 4 | human operator/input device |
| PATIENT EQUIPMENT i.e. Bed Status etc. | 5 | automatically/input device |
| CHAIR | 6 | human operator/input device |
| PRIORITY PATIENT | 6 | human operator/input device |
| PATIENT | 7 | human operator/input device |
| STAFF | 8 | human operator/input device |

A SMOKE ALARM call indicates sensed smoke, representing a fire hazard. A CODE BLUE represents an immediate life-threatening condition with respect to a patient. A STAFF EMERGENCY represents an urgent need by one nurse or staff member for assistance from one or more other nurses or staff members. A BATHROOM call is generated by a patient, and it indicates a higher priority of need than a normal PATIENT call, due to the increased possibility of danger or the more urgent need for assistance while in the bathroom. A SHOWER call is similar to a BATHROOM call, but it is generated at a different location in the bathroom of the patient room, i.e. the shower stall. A PATIENT EQUIPMENT calls represents a malfunctioning component of the system, or a status signal related to a patient or bed monitoring apparatus. A CHAIR call is basically a patient call generated remotely, as by an IR transmitter. A PRIORITY PATIENT call indicates that the call originated from one patient who is a member of a preferred class of patients, for one reason or another. A PATIENT call indicates a normal or standard patient call to the system. A STAFF call indicated a non-urgent call placed by a nurse or staff member.

II. The Hardware

Figure 1:
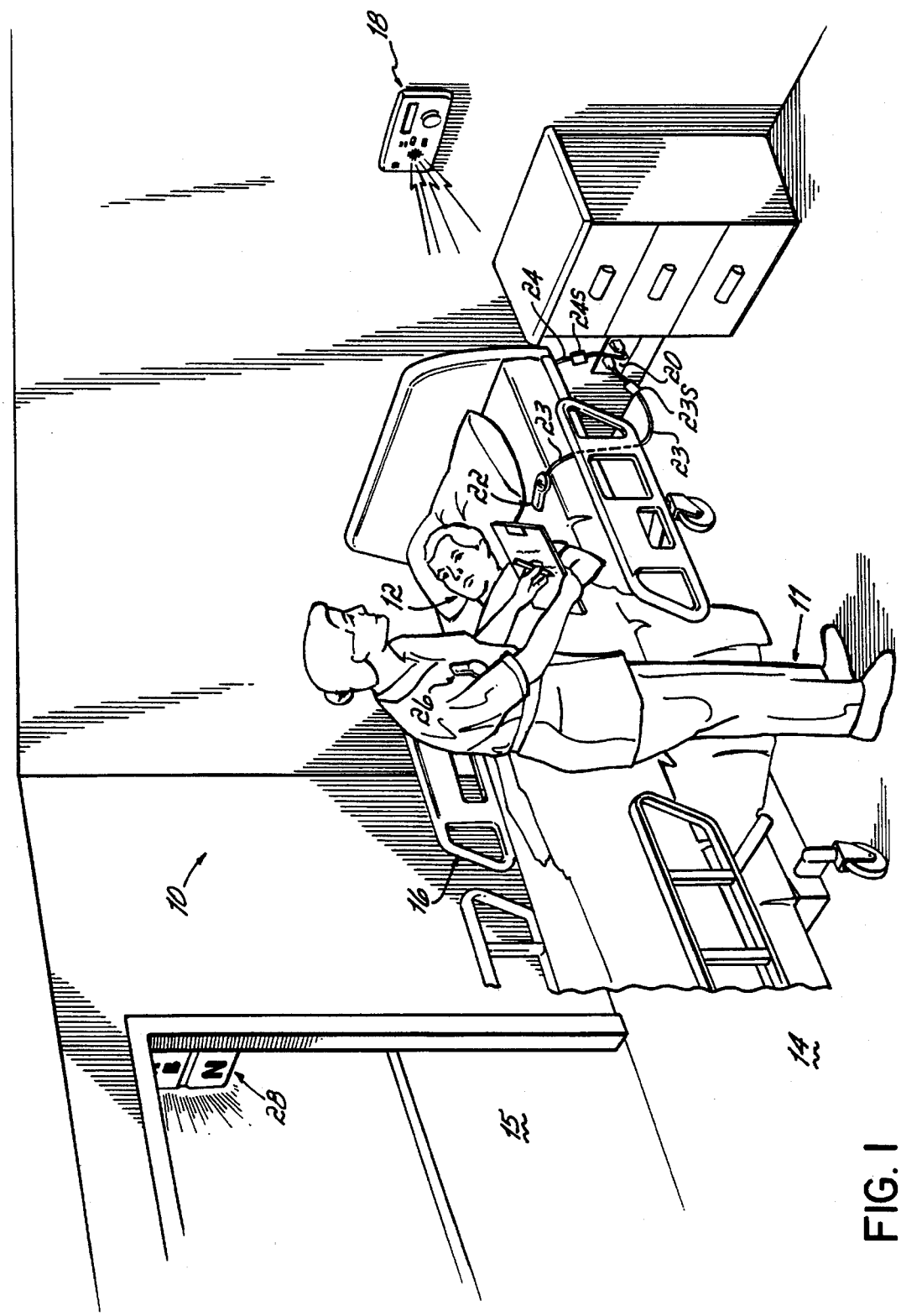
FIG. 1 is a perspective view of a portion of a hospital room which illustrates one patient station in a patient room and the physical arrangement of some of the other components of a patient/nurse call system in accordance with this invention.

FIG. 1 shows a physical layout of some of the components of a patient/nurse system 10 constructed in accordance with a preferred embodiment of the invention. A patient/nurse call system 10 of this invention organizes, stores, maintains and facilitates retrieval of the various calls placed in a hospital wing or ward, thereby optimizing communication capabilities among nurses 11 and patients 12.

More specifically, FIG. 1 shows a patient room 14 accessible from a hall 15 of the hospital wing, and a hospital bed 16 located in the room 14. While only one bed is shown, the invention contemplates semi-private patient rooms 14, wherein two patient beds 16 are used. Additionally, if desired, the system 10 can be configured for more than two beds 16 in a single room 14. A patient station 18 is mounted to a head wall of the patient room 14.

The patient station 18 is connected by a hardwire connector 21 (not shown in FIG. 1) to a bed receptacle controller 20, with connector 21 located behind the headwall of the room 14. A pillow unit 22 connects via cable 23 to a bed outlet or plug 23p of the receptacle 20. Additionally, a first end of a bed cable 24 plugs into a bed outlet or plug 24p of the receptacle 20, and a second end of the cable 24 connects to a bed status controller (not shown) for the hospital bed 16. Near outlet 20, cable 23 and cable 24 include switches 23s and 24s, respectively. These switches enable the cables 23 and 24 to be unplugged without generating an equipment alarm call, referred to as a PATIENT EQUIPMENT call. Preferably, these switches are dual position for deactivating or activating an automatic alarm built into the outlet 20. The alarm is always activated unless the switch has been switched open. The alarm remains deactivated a predetermined number of seconds after switching, and then it reactivates. This automatic alarm for pillow units 22 is standard in many hospitals, and nurses 11 have come to instinctively pull the connector from the pillow unit 22 if they need help in a hurry. The switches 23s and 24s allow the system 10 to accommodate this common practice.

FIG. 1 also shows a badge 26 worn by a nurse 11. The badge 26 clips to the outside of clothing worn by the nurse 11. The badge 26 transmits a pulse-coded signal, preferably infrared, which is received by a receiver 121 which is preferably located at the patient station 18, so that the system 10 can determine and continuously update locations of nurses 11 on duty within the hospital wing.

Figure 2:
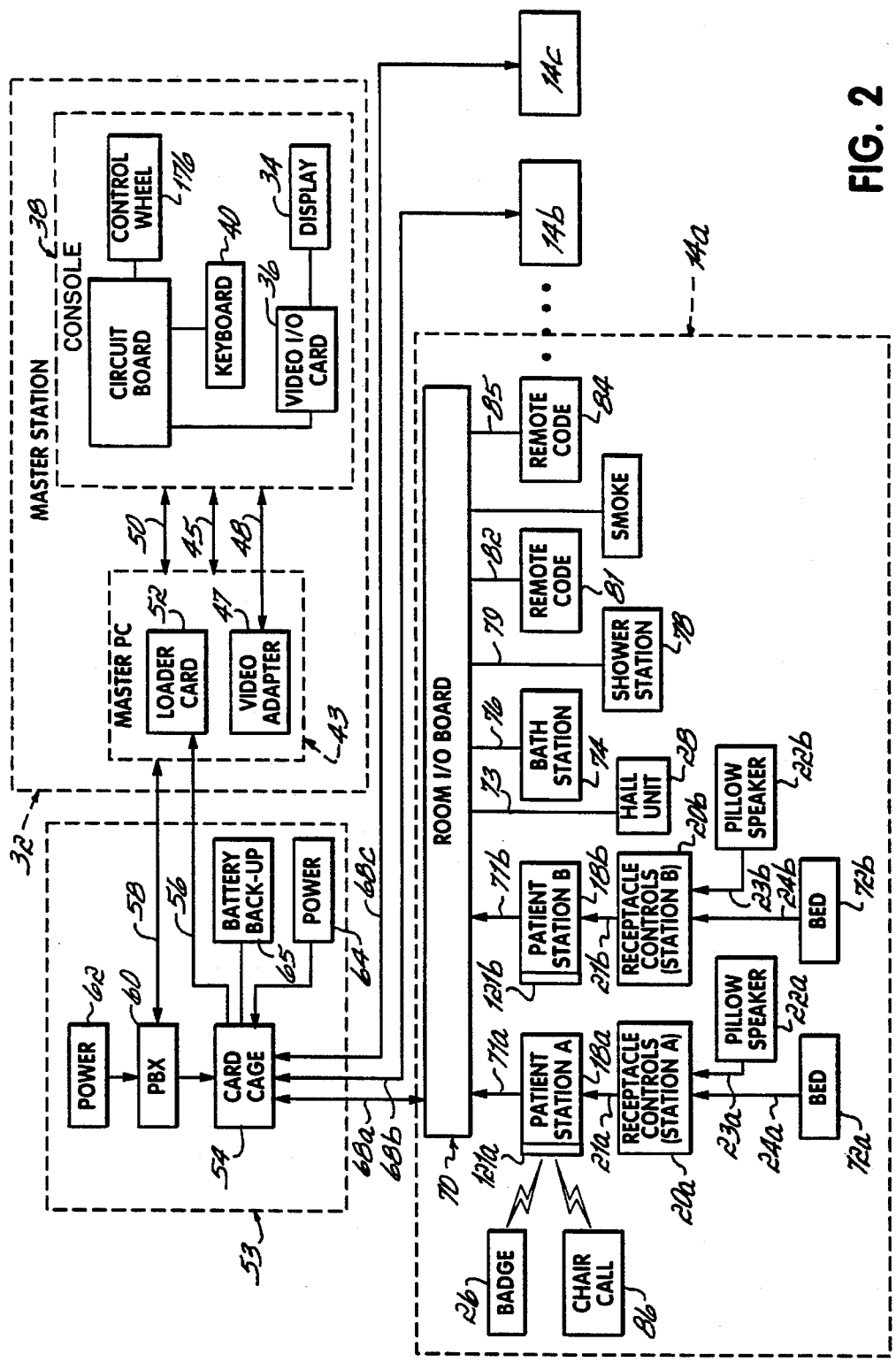
FIG. 2 is a schematic which generally depicts the electrical interconnections among the components and stations of the patient/nurse call system of this invention.

FIG. 2 schematically illustrates electrical connections among hardware components according to a preferred embodiment of the system 10. More specifically, FIG. 2 shows a master station 32 which interconnects with all of the patient stations 18. At the master station 32, the system 10 stores location information about the nurses 11, information about hospital calls, information about hospital beds in use, the status of the hospital beds in use, instructions on how to operate the system 10, and a number of other features. The master station 32 classifies and displays the hospital calls according to priority status and according to time received. When the calls are retrieved by the patient stations 18, they are retrieved in this same order.

Structurally, the master station 32 includes a color LCD display 34, a video I/O card 36, a keyboard 40, a control wheel 176, an acoustical speaker 178 and a handset 179 which interconnect with a master station console 38. The master station console 38 serves as the interface between these components and a master station personal computer 43 which preferably includes memory, a hard drive (with at least 4M byte memory capacity), a floppy disc drive, parallel ports, serial ports and a power supply. A keyboard cable 45 interconnects the master station console 38 with a video adapter 47, preferably a Yamaha card. A coaxial cable 48 supplies electrical power to master console 38 and these components, and cable 48 interconnects the video interface 36 with the video adapter 47, via master station console 38. Another electrical cable 50 interconnects the master station console 38 with a loader card 52 in the personal computer 43, and cable 50 includes two audio (2B+2D) channels in a single, eight conductor wire. The master station 32 is physically located at a staff station in the hospital wing, a nurse station of the hospital wing or a general office for the hospital wing.

The personal computer 43 of the master station 32 interconnects via cables 56 and 58 to signal processing components of the system, which are preferably located within an equipment closet or cabinet 53 in the hospital wing. Cable 56 includes three audio (2B+2D) channels in a single, eight conductor wire, and cable 58 is an RS-232 line. The components located within the equipment cabinet 53 include a card cage 54 for locating power distribution cards (not shown) and an expandable private branch exchange (or "PBX") 60, which is preferably a component manufactured by Comdial Corporation of San Francisco, Calif. under the trademark DXP.

Basically, this DXP is a voice/data switch, and it contains the necessary hardware and software to allocate point-to-point audio links and to distribute data in the form of messages from the master station 32 to the patient stations 18, and vise versa.

The master station 32 occupies three audio stations. A single DXP serving as the PBX 60 can connect five 15-channel cards, or seventy-seven patient stations plus the master station 32. Each power distribution card in the card cage 54 can connect a maximum of sixteen audio stations. An expanded PBX 60 and cabinet 53 can allow a total of one hundred and ninety-two audio stations or one hundred and eighty nine patient stations 18 plus one master station 32 (which requires three audio lines). This expanded capability requires one PBX (type DXP) 60, a DXP expansion cabinet (not shown) and twelve power distribution cards. Eventually, interconnection of additional master stations 32 could further expand the capability of the system 10.

A power supply 62 supplies electrical power to the PBX 60. A power supply 64 and a battery backup 65 connect to card cage 54 and supply electrical power to the other components in the cabinet 53.

An electrical cable 68 connects one of the power distribution cards of the card cage 54 to a patient room I/O board 70. Each hospital room 14 in the hospital wing includes an I/O board 70, and this I/O board 70 includes multiple connections and inputs for generating calls from the room 14. FIG. 2 shows patient room 14a connected to card cage 54 via cable 68a, and patient rooms 14b and 14c connected via cables 68b and 68c, respectively.

The I/O board 70 and its interconnected components comprise the intra-room network. Communication among components connected to I/O board 70 occurs over two wire, half duplex, multidrop EIA RS-485 standard, with message exchange being peer to peer. Any device on the intra-room network can send data to any other device without waiting for a poll. The intra-room network is not transformer isolated.

Each patient station 18 interfaces with the PBX 60 over a two-wire twisted pair network (Motorola UDLT 2B+2D), and messages are transmitted and received between the stations 18 and the PBX 60 over the D-channel. Messages received by the PBX 60 from the patient stations 18 are transmitted to the master station PC 43, and messages received by patient stations 18 originate at the master station PC 43. Patient stations 18 cannot send messages directly to each other. A patient station 18 and/or the master station PC 43 can transmit a message at any time. At the master station PC 43, a COMDIAL-supplied library called the ENTERPRZ handles the interface with the PBX 60. All messages that the system 10 wishes to pass to a patient station 18 are converted to a form that the ENTERPRZ library can accept. The ENTERPRZ library has only one function, for passing messages to stations 18 on the network. This function can only accept 16 bytes of information at a time, and the bytes must be printable ASCII characters. The destination address is also passed as part of this function. The ENTERPRZ library then embeds this information into it's own link-level protocol, with it's own control information, including destination, address and checksum, etc., and sends it as a packet to the PBX 60.

With respect to patient room 14a shown in FIG. 2, patient stations 18a and 18b connect to the I/O board 70 via cables 71a and 71b, respectively. Bed receptacles 20a and 20b connect to stations 18a and 18b via cables 21a and 21b, respectively. Cable 24a interconnects a bed status controller 72a to the bed receptacle 20a, and cable 23a connects the pillow unit 22a to the bed receptacle 20a. Patient station 18b includes similar connections.

Additionally, hall unit 28 connects to the I/O board 70 via connector 73. Bath, or bathroom, station 74 connects to I/O board 70 via connector 76. Shower station 78 connects to I/O board 70 via connector 79. Remote code station 81 connects to I/O board 70 via connector 82. Remote staff station 84 connects to I/O board 70 via connector 85.

Bath station 74, shower station 78, remote code station 81 and remote staff station 84 are adapted to be actuated to generate BATHROOM, SHOWER, CODE BLUE and STAFF calls, respectively, to the system 10 from patient room 14a. With respect to bathroom station 74 and shower station 78, the calls generated are assigned a higher priority than a normal patient call generated by the pillow speaker. This is due to the increased urgency associated with a patient's need for help when in the bathroom, and an even higher need for urgency when in the shower. Remote code station 81 generates a code blue call. Remote staff station 84 generates a staff call. Additionally, each of patient stations 18a and 18b also permits generation of a CODE BLUE call and a STAFF EMERGENCY call.

Additionally, FIG. 2 shows one of the nurse-worn badges 26 which communicates with the patient station 18a via infrared signaling. The system 10 may include a chair call device 86 which also communicates with the patient station 18 via pulsed infrared signaling. The chair call device 86 may be used by a patient 12 to generate a call, designated a CHAIR call, when he or she is away from the pillow unit 22.

Figure 3:
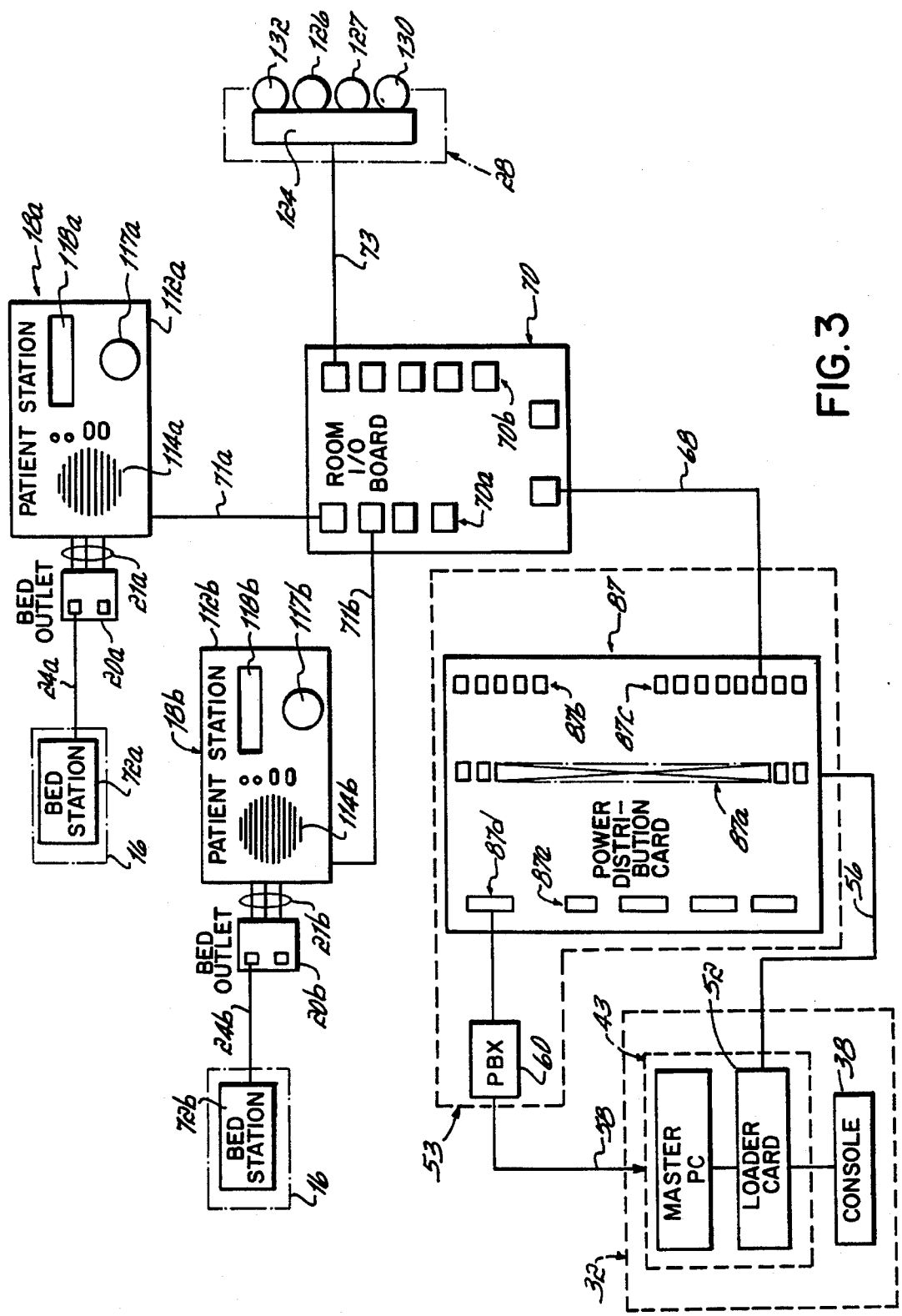
FIG. 3 is a schematic which depicts the electrical wiring for a semi-private patient room interconnected to the patient/nurse call system of this invention.

FIG. 3 is a schematic wiring diagram which shows the connections between the master station 32 and a patient room 14, but in somewhat more detail than FIG. 2. More specifically, FIG. 3 shows one of the power distribution cards 87 housed within card cage 54 (FIG. 2). Each power distribution card 87 includes twenty one-channel ports 87a, five three-channel ports 87b, eight two-channel ports 87c, a data port 87d which connects to the PBX 60, and four parallel power ports 87e. Distribution card 87 also includes a plurality, preferably 20, one-amp fuses (not shown) with each fuse corresponding to one of the single channel parts 87a. Preferably, cable 56 connects the bottommost of the single channel ports 87a to the loader card 52. In this configuration, the two lowest two-channel ports 87c cannot be used. Moving upwardly from the bottommost of the one-channel ports 87a, the next three ports are designated loader, master voice, and master monitor. The uppermost of the one-channel ports 87a is designated as a booster port.

The ports of the power distribution card 87 designate the addresses for the patient stations 18. Between the power distribution cards 87 and the various stations 18 within the room 14, i.e., the intra-room network, the call signals and nurse information signals do not include an address or a location signal. When calls are generated within the patient rooms 14, each call is routed to the distribution card 87 via the port designated for that specific station 18, and the signal is further conveyed from the power distribution card 87 to the master station 32, but with a signal address appended thereto by the PBX 60 to designate the specific station 18. Signalling between the PBX 60, the loader card 52 and the master station 32 is via a serial data string on an RS-232 line, and each data string includes call information (or nurse location information) combined with location information related to a particular patient station 18. The interconnection between the loader card 52 and the bottommost of the single channel ports 87a is used to download software instructions from the master station 32 to the I/O boards 70 and the stations 18. This feature will be described in more detailed in a later section.

As shown in FIG. 3, the I/O board 70 for a patient room 14 provides an interface between the power distribution cards 87 and the stations 18 and hall units 28. More specifically, each I/O board 70 includes a plurality of ports 70a, each of which may be connected via a cable 71 to a patient station 18. Additional output ports 70b are configured to be connectable to the hall unit 28 via a connector 73. Ports 70a or 70b may also be used for one or more additional stations such as a bath station 74, a shower station 78, remote code station 81 or remote staff station 84, depending upon the needs of the particular hospital wing.

Figure 4:
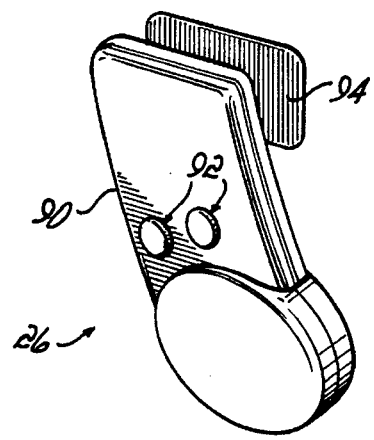
FIG. 4 is a perspective view of a pulse transmitting badge for a patient/nurse call system constructed in accordance with this invention.

FIG. 4 is a perspective view of a transmitting badge 26 worn by nurses 11 assigned for duty within the hospital wing, in accordance with a preferred embodiment of the invention. The badge 26 includes a housing 90, which is preferably made of molded plastic, two light emitting diodes 92 for transmitting pulse-coded infrared signals, and a spring biased clip 94 which enables the badge 26 to be clipped to the clothing of the nurse 11. The badge 26 weights about one ounce and it is approximately 2.75"×1.25"×0.5". The badge 26 transmits a pulse-coded, modulated infrared packet every six to eight seconds. The pulses are of fixed length and fixed amplitude.

Figure 5:
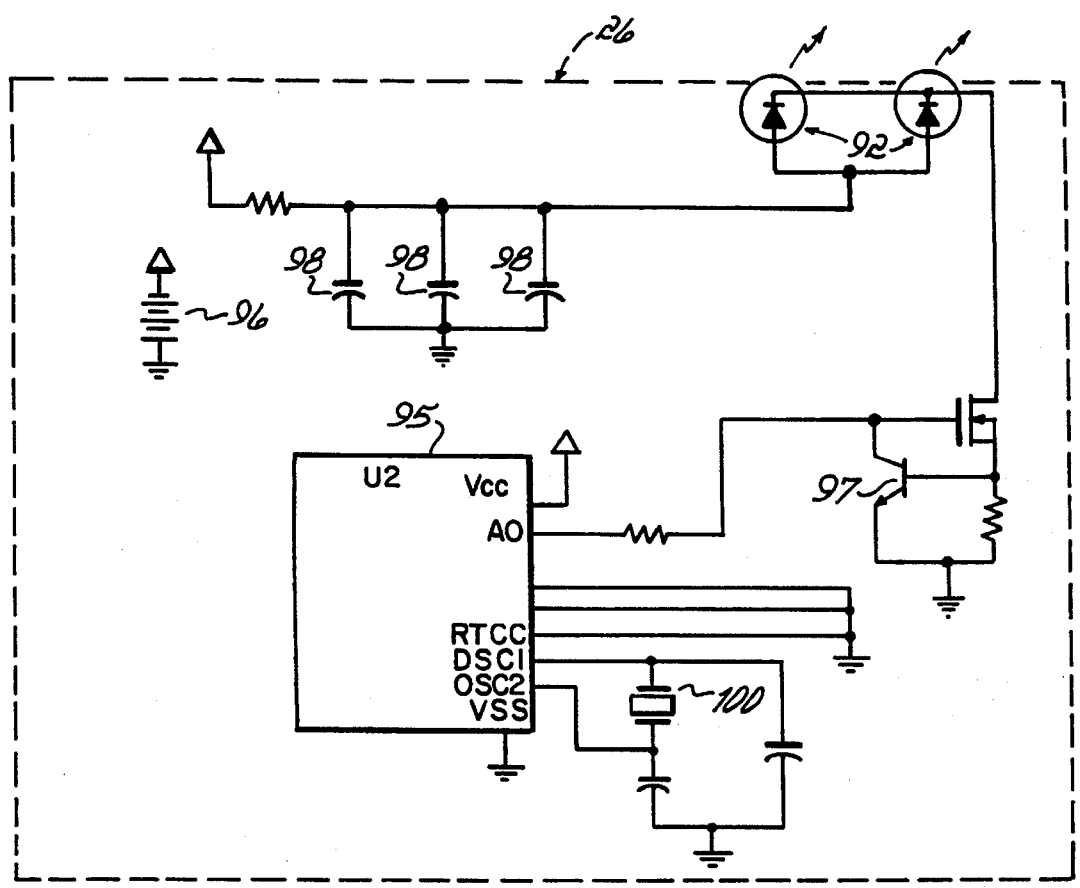
FIG. 5 is an electrical schematic of the badge shown in FIG. 4.

FIG. 5 is an electrical circuit schematic which shows the components and interconnections among the components of the badge 26, which preferably transmits pulsed-coded infrared signals(≈940 nm wavelength). According to the invention, a pulse or lack of a pulse within a prescribed time slot represents either a logic 1 or a logic 0. A pulse (logic 1) comprises several cycles of a 36 kHz signal. Each packet comprises 27 total bits, including a start bit, 13 data bits and 13 inverted data bits. Transmission of the same 13 data bits but in inverted condition insures integrity of the packet. If desired, additional start bits may be used.

Use of 13 data bits allows for 8,192 unique code numbers. Some of the code numbers may be reserved for future applications, while a number of the code numbers are dedicated solely for the purpose of nurse identification. The 13 data bits which identify the particular badge 26 are preferably stored internally in an EPROM located in the badge 26.

The following table identifies internal components of the badge 26 which applicant has used successfully.

TABLE II

| MANU-FACTURER | MODEL # | ITEM | DESIGNATION # |
|---|---|---|---|
| MicroChip | PIC16C54 | Microcontroller | 95 |
| Sanyo | CR2450 | Battery | 96 |
| Siemens | SFH409-3 | IR LEDs (2) | 92 |
| Motorola | MTD3055EL | FET | 97 |
| Illinois Cap. | 470uF6VDC | Transistor (3) | 98 |
| National | 2N2222 | Transistor | 99 |
| Murata Erie | 2Mhz | Resonator | 100 |

These components are mounted on a printed board, which may be a PCB made by DSI.

The microcontroller 95 has a power saving mode (about 14 microamps) that is referred to as "sleep". During sleep, a watchdog timer continues to run and will "wake up" the microcontroller 95 after approximately two seconds. Since the badge 26 transmits the signal approximately every six seconds, there is a sleep count register initially set to two spaces. Each time the microcontroller 95 "wakes up", it checks the sleep count register to determine if six seconds have expired. If six seconds have not expired, the microcontroller 95 decrements the sleep count and goes back to sleep. If six seconds have expired, i.e., the sleep count is zero, and the microcontroller 95 reads the 26 bits of internal memory that contain the encoded identification number. Initially, the start or parity bit is clocked out and is then followed by the 26 data bits. The microcontroller 95 generates the 36 kHz carrier and the timing for each bit. The field effect transistor 97 and the transistor 99 drive the two LEDs 92 which emit the infrared signal packet. After a packet has been sent, the sleep count is reinitialized and the microcontroller 95 goes back to sleep. If it is desired to transmit from the badge 26 less frequently, perhaps every eight seconds, the sleep count register is initially set to three spaces.

The battery 96 for the badge 26 is designed to operate continuously for four months. The particular battery 96 chosen for this badge 26 requires an industrial grade (500 mAh+) CR-2450, due to its power capabilities.

The chair call 86 can be made by modifying the circuitry of the badge 26 to include an OFF/ON switch so that transmission is not continuous, and by programming a different code, i.e., a CHAIR call, into an EPROM housed therein.

Figure 6:
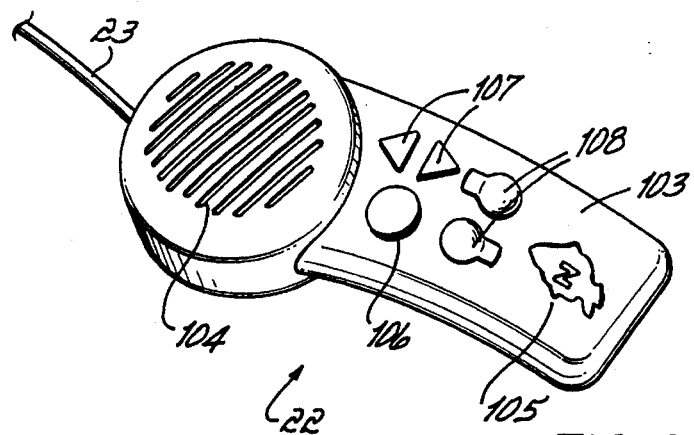
FIG. 6 is a perspective view of the pillow unit for a patient/nurse call system in accordance with this invention.

FIG. 6 shows a perspective view of a pillow unit 22. The pillow unit 22 operatively connects to outlet 20 via connector 23. The pillow unit 22 includes a molded plastic housing 103, acoustical speaker 104 and a nurse call button 105. Depression of nurse call button 105 generates a patient call from the respective patient station 18. Preferably, the pillow unit 22 further includes a television on/off power button 106, channel selectors 107 and light switches 108. Additional controls may include light dim switches and television volume controls. These signals may be transmitted along conductors routed within connector 23, or they may be IR signals.

Figure 7:
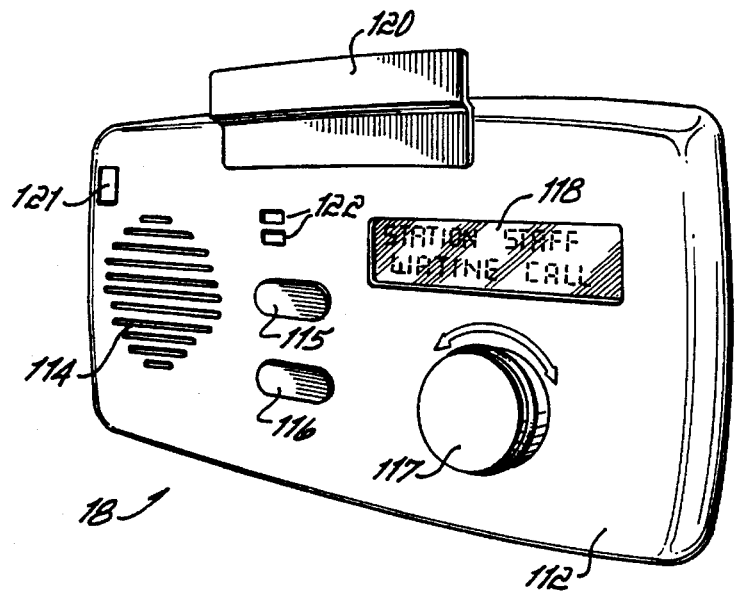
FIG. 7 is a perspective view of a patient station for a patient/nurse call system in accordance with this invention.

FIG. 7 shows a perspective view of the patient station 18. The patient station includes a molded housing 112 which connects to the head wall, preferably by screws. An audio speaker 114 resides on the left side of the housing 112. Pushbutton 115 generates a staff emergency call, and pushbutton 116 cancels the call. Control wheel 117 operates in conjunction with a display 118 to control retrieval of information from the master station 32 for display at the patient station 18. Preferably, the display 118 is a two-line by sixteen character LCD display.

More specifically, display 18 includes a curser which points to one of three designations, STATION, STAFF, WAITING CALL. Rotation of the control wheel 117 moves the curser between these three designations. With the curser pointing at one of the designations, depression of the control wheel 117 selects the function represented by that designation. If WAITING CALL is selected, the patient station 18 displays the unanswered calls stored in the system 10 at the master station 32. Because of the limited amount of space on display 118, the user must rotate control wheel 117 to scroll the waiting calls. If STAFF is selected, the display 118 visually indicates all staff presently on duty in the hospital wing, plus the current, stored location information for the nurses 11 derived from the badges 26. If STATION is selected, a STAFF call is initiated.

The user interface for the patient station 18 is menu driven, and this interface is more fully explained in Appendix B of Section III, entitled "Operation".

The patient station 18 further includes a receiver 121 adapted to receive the pulse-coded signals transmitted from the badges 26 and thereby generate location signals for nurses 11 wearing the badges 26. If desired, the housing 112 may also include one or more LEDs 122 which indicate one or more of the following conditions, a call placed from the station 18, audio channel open to the station 18 or receipt of an IR signal from a badge 26.

The microcontroller connected to the receiver 121 performs three tasks. It receives, decodes and validates pulsed signals from the badges 26. It maintains the status of the identification signals generated in response to receipt of the IR signals, and communicates the status information to the other components of the intra-room network for the particular station 18, namely, one of the indicator lights on housing 112, the indicator lights 126 or 127 at hall unit 128, and input/output board 70.

Upon initial receipt of a signal from a badge 26, a microcontroller of the receiver 121 starts a bit timer (after delaying for one half of a valid bit width). After the bit timer expires, the receiver 121 samples the signal from the front end. If the signal is HIGH, the bit is a 1, if the signal is LOW, the bit is 0. Sampling continues for all consecutive bits. The microcontroller must receive a thirteen bit string which is matched by a subsequent thirteen bit string, but inverted, for the packet to be valid. If a start bit is received but no data or invalid data is received, receiver 121 considers this to be noise or a "packet collisions" between other badges 26 and no signals are validated.

For each valid identification signal received, a separate timer keeps track of its presence. Each time an existing identification signal is received, the timer for that signal is reset to zero. If the timer reaches thirteen seconds without receiving a subsequent signal, i.e., two consecutive transmissions if transmission occurs every six seconds, the system 10 assumes that the nurse 11 wearing that badge 26 has left the room 14, and that particular identification signal is deleted from the table. If there is at least one identification signal registered for a room 14, and an invalid packet is received, the software for the receiver 121 assumes that the received invalid signal was an attempt to update the table. As a result, for each of the identification signals in the table, the timer is set to zero as if a valid packet has been received. However, this may only happen once before another valid signal is received. Otherwise, receiver 121 deletes the identification signal from the table. Thus, normal operation requires that the nurse 11 be out of the room 14 for a maximum of thirteen seconds before "checking the nurse out" i.e., deleting him or her from the table, or upon receipt of the nurse's signal at another station, whichever occurs first.

The top of housing 112 includes a lever 120 for generating a CODE BLUE CALL. Preferably, this lever 120 requires two separate movements, or movements in two distinct directions, to reset. A CODE BLUE call cannot be cancelled.

The design and arrangement of the components of the patient station 18 facilitates nurse 11 interaction with this patient/nurse call system 10. Use of nurse locating badges 26 in combination with the display 118 and the control wheel 117 optimizes information flow and verbal exchanges among nurses 11 on duty within a hospital wing. Thus, the system 10 utilizes nurse locator badges 26 to help nurses 11 become more efficient in their duties, rather than simply monitoring their whereabouts.

Although the receiver 121 is mounted within housing 112 of a patient station 18, it may be physically removed therefrom and placed in a more convenient location for detecting signals from the badges 26, if desired. The receiver 121 is preferably an infrared receiver, (such as a Siemens Model Number SFH-506-36), which provides automatic gain control, band pass filtering, demodulation and wave shaping. Thus, the output of receiver 121 may be routed directly to an interrupt input of a microcontroller (not shown) for the patient room 14. The receiver 121 maintains a table of all badges 26 located in the room 14. When a badge exits a room 14, the receiver 121 adjusts the table and informs the system 10 of the change. Because this table is maintained locally, i.e., at the locator receiver, only changes in the table are signaled to the station 18 and the rest of the system 10.

Figure 8:
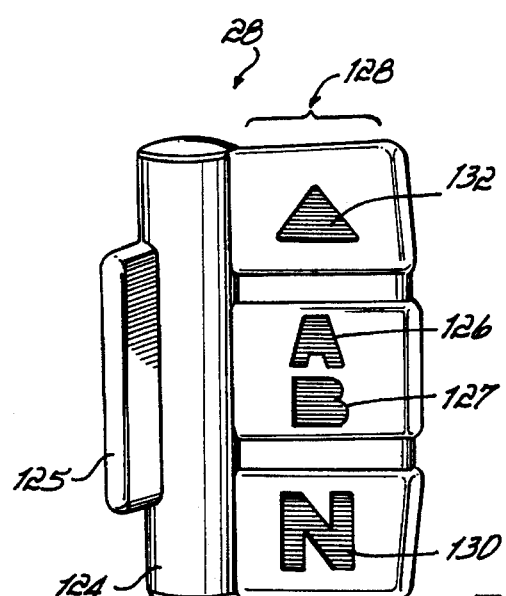
FIG. 8 is a perspective view of a hall unit for a patient/nurse call system in accordance with this invention.

FIG. 8 shows a hall unit 28 located outside each patient room 14 in the hospital wing. The hall unit 28 includes a molded housing 124, which includes a base or mounting plate 125 and a protruding section 128 which includes indicator lights 126 and 127 for indicating when patient calls have been generated at patient stations 18a and 18b, respectively, and an indicating light 132 which illuminates upon generation of a CODE BLUE call, a STAFF EMERGENCY call, a BATHROOM call or a SHOWER call. Preferably, indicating light 132 flashes according to one of a number of different predetermined patterns or sequences, with each pattern dedicated one of these "higher priority" calls. Additionally, an audible alarm may also sound to indicate one of these higher priority calls.

An indicating light 130 illuminates when a signal from a badge 26 has been received by the receiver 121. Preferably, upon receipt by the receiver 121 of an infrared signal from a badge 26, the patient station 18 automatically cancels any PATIENT call placed from that particular station 18. This cancels illumination of indicating light 126 or 127, depending upon the particular station 18. Thus, nurse presence in the room 14 is indicated via illumination of an indicating light 130 located in the hall 15 and/or another indicating light mounted to housing 112 at the station 18.

Additionally, each of the lights of the hall units 28 may include a test button which, when depressed, actuates the lights, thereby to indicate to nurses that the hall unit 28 is operating correctly. Alternatively, an LED associated with each light of the hall unit may activate upon sensing a burnt out condition. If desired, this signal may also be conveyed to the master station 32.

FIG. 9 shows a bathroom station 74. Preferably, the station 74 includes a housing 134, a pull bar 135 and a slide 136 connected to the pull bar 135. A patient's pulling of the pull bar 135 will initiate a BATHROOM call, or a SHOWER CALL. The station 74 may also include a pushbutton 137 for cancelling the call.

FIG. 10 shows a hospital bed 16 interconnected with the patient/nurse call system 10 of this invention. The bed 16 includes a headboard 140, a footboard 141, head siderails 143, foot siderails 144 and a mattress having head and foot ends 146 and 148, respectively. The mattress may be covered intermediate ends 146 and 148 by an incontinence detection pad 147. The mattress preferably can be inflatable and can be raised, lowered or anchored. Bed 16 also includes a plurality of sensors which sense conditions in the bed 16. These conditions may include, but are not limited to, ground fault, bed down, brake not set, bed power, head or foot end raised 30° or higher for longer than a prescribed time, mattress excessive air loss, bed exit armed, bed exited, head or foot siderails latched or incontinence detected, as disclosed in applicant's co-pending U.S. patent application Ser. No. 08/145,767, filed on Oct. 29, 1993, entitled Incontinence Detection Device, which is expressly incorporated by reference herein in its entirety.

All of the bed status sensors generate signals which are fed to a bed control unit 149. This control unit 149 may include visual displays for indicating the status of the bed 16 at the footboard 141. In accordance with this invention, the bed control unit 149 also connects, via cable 24, to the bed outlet 20, and the bed status signals are transmitted to master station 32 for storage and subsequent retrieval. An operator at the master station 32 may determine the status of each of the bed conditions and react accordingly, if necessary.

Preferably, each bed 16 also has a serial number assigned thereto during manufacture. This serial number may be read from the bed 16 to the master station 10 so that the system 10 can keep track of the location and amount of use for each bed 16, and/or maintenance performed or needed over the useful life.

Figure 11A:
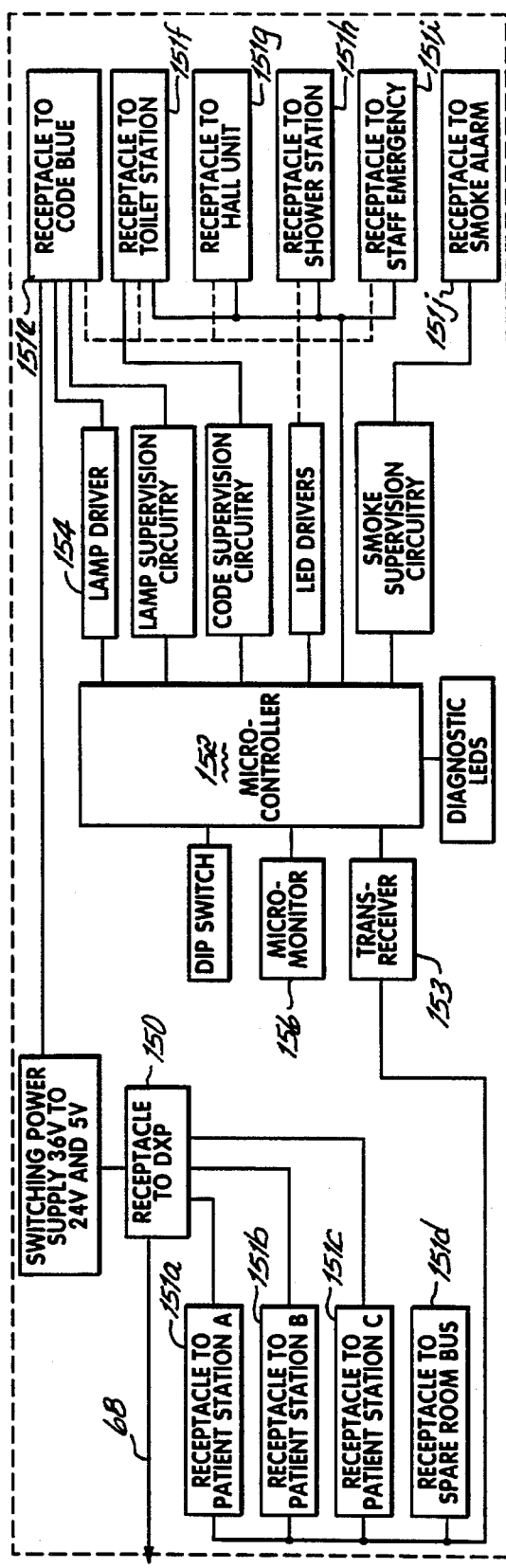
FIG. 11a is an electrical schematic which shows the electrical connections among the components of the hall unit for a patient/nurse call system in accordance with this invention.

FIG. 11A shows electrical connections for components of I/O board 70. More specifically, the I/O board 70 includes a receptacle 150 which interconnects with the PBX 60. RJ45 Receptacles 151a, 151b and 151c are adapted to be connected with inputs from patient station 18a, 18b and 18c, respectively (for a room with three stations). An additional receptacle 151d is reserved for a spare room bus. If a patient room 14 only includes two stations 18, the receptacle 151c would serve as an additional spare.

The I/O board 70 further includes a microcontroller 152 and additional RJ45 receptacles 151e, 151f, 151g, 151h, 151i and 151j for interconnection with the hall unit, an additional CODE BLUE station, a BATHROOM, (or TOILET) station, the SHOWER station, the STAFF EMERGENCY station and the SMOKE ALARM station, respectively. In conjunction with a transceiver 153, the microcontroller 152 communicates with the stations 18a, 18b and 18c to control operation of lamp drivers 154 which control actuation of the lights, 126, 127, 130 and 132 at the hall unit 28.

FIG. 11A also shows that a CODE BLUE receptacle 151f, the BATHROOM receptacle 151g, the SHOWER receptacle 151h and the STAFF EMERGENCY receptacle 151i also interconnect with hall unit receptacle 151e and LED drivers 155. This permits actuation of light 132 at the hall unit 28 upon generation of a CODE BLUE call, a BATHROOM call, a SHOWER call or a STAFF EMERGENCY call, respectively from the patient room 14. The microcontroller 152 and LED drivers 155 control operation of light 132 so that it flashes according to a predetermined sequence which is unique to the type of "higher priority" call which has been generated.

Thus, a nurse 11 in the hallway 15 may readily determine which of these "higher priority" calls has been generated from the room 14. In addition to flashing of light 132 according to a predetermined sequence which corresponds to the high priority call that has been generated, an audible alarm may also be sounded, with the sounds actuated according to tone and/or sequence in a predetermined manner, thus enabling a nurse 11 to audibly identify which type of high priority call has been generated from the room 14.

Figure 11B:
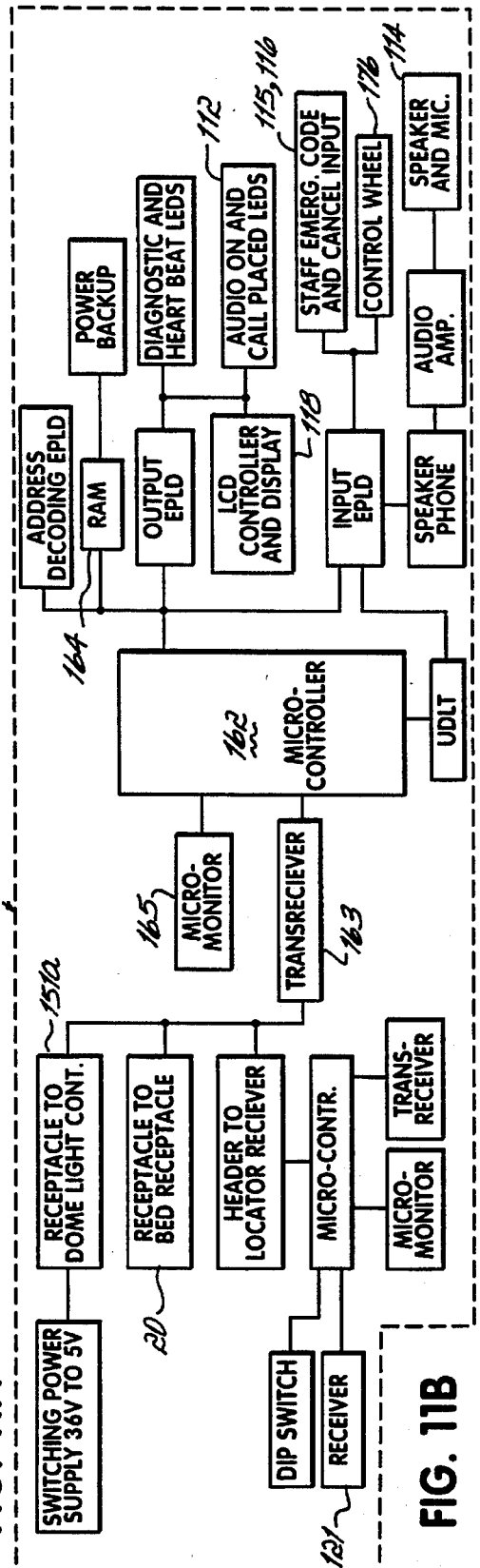
FIG. 11b is an electrical schematic which shows electrical connections among components of the patient station for a patient/nurse call system in accordance with this invention.
Figure 11C:
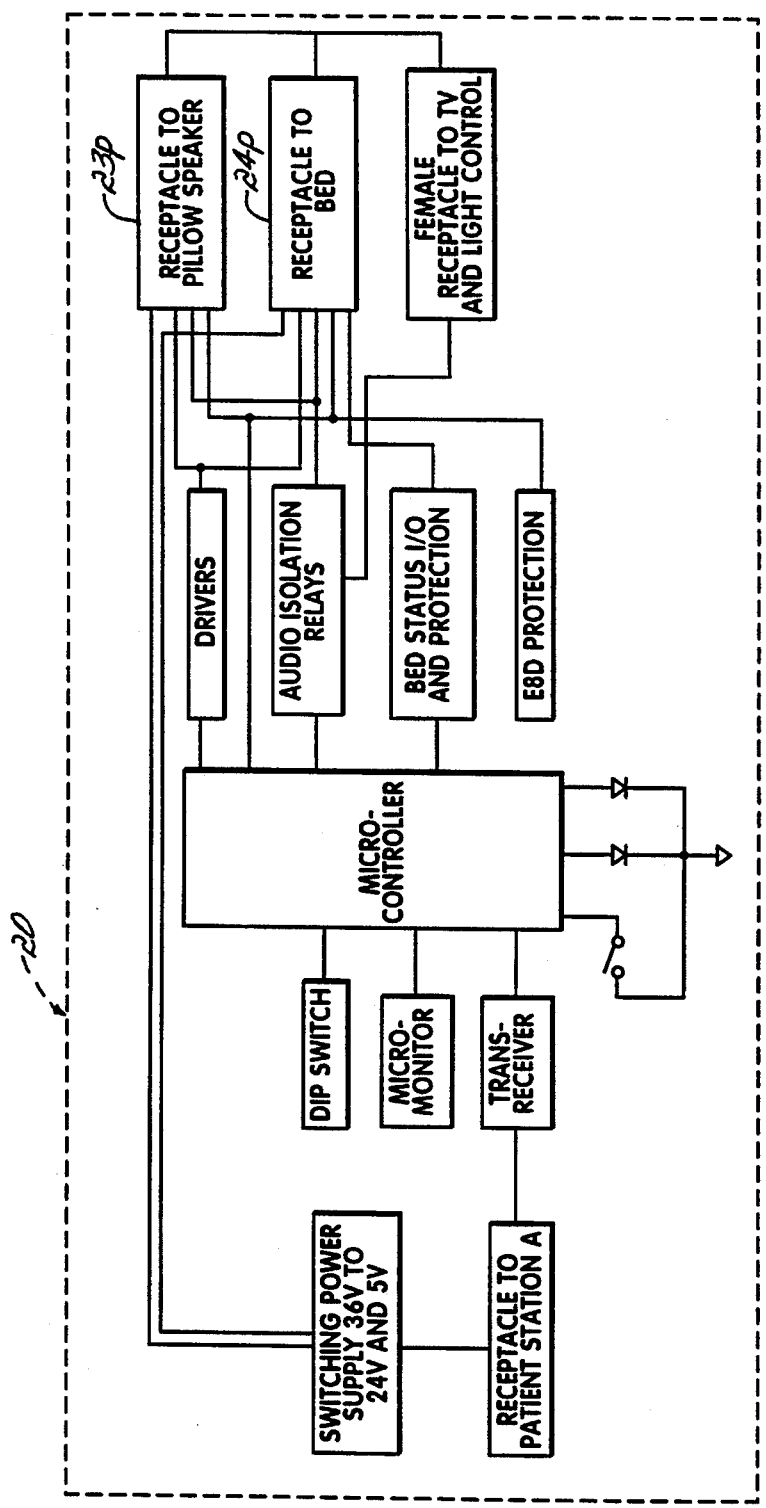
FIG. 11c is an electrical schematic which shows electrical connections among components of the bed receptacle controller for a patient/nurse call system in accordance with this invention.

FIG. 11B shows the electrical interconnections at each of the patient stations 18. Operations at the patient station 18 are controlled by a microcontroller 162 which communicates with other components of the I/O board 70 via a transceiver 163. Preferably, the microcontroller 162 is an Intel 87C52, and the transceiver 163 is a Linear Tech LEC485. Microcontroller 162 of the patient station 18 controls operation of the inputs and the outputs mounted to housing 112. Patient station 18 also includes a random access memory designated 164, and a micromonitor 165, which is preferably a Dallas DS1232.

FIG. 12 shows a perspective view of a master station 32 for the patient/nurse call system 10 of this invention. The master station 32 includes a display 34, which is preferably a color liquid crystal display, a retractable keyboard 40 which slides underneath the control panel 174, a rotatable control wheel 176 which mounts to the panel 174 and an audio speaker 178 which also mounts to the panel 174. Master station 32 also includes a handset 179.

With calls displayed on display 34, lifting the handset 179 initiates an audio link with the patient station 18 which generates the highest priority call stored at the master station 32. If the control wheel 176 is rotated to "highlight" a different call, and the control wheel is then depressed, a two way audio link is established with the patient station 18 which generated the "highlighted" call.

Figure 13:
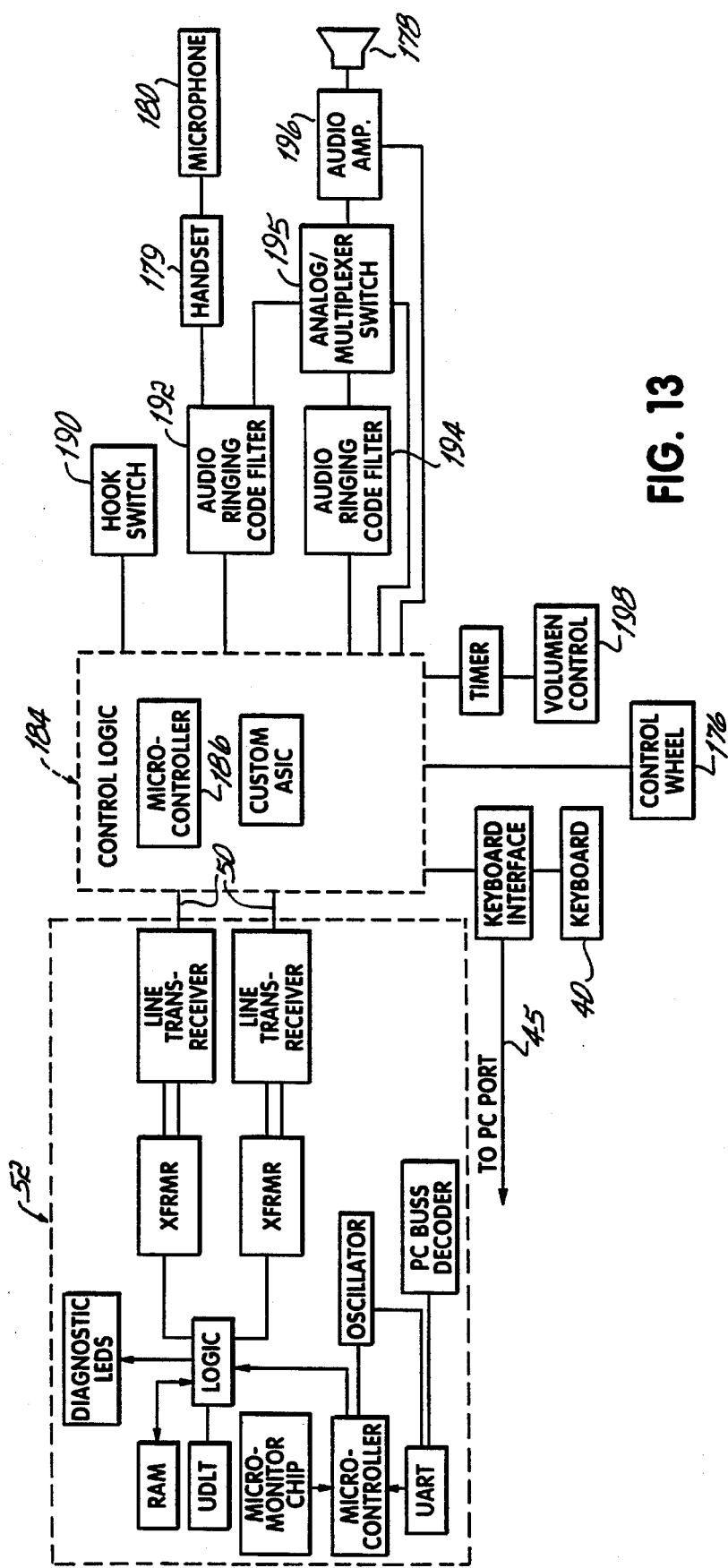
FIG. 13 is an electrical schematic of a portion of the master station for a patient/nurse call system in accordance with this invention.

FIG. 13 shows electrical interconnections among the non-video components at the master station 32. Block 184 designates the control logic for controlling operations at the master station 32. This includes a programmable microcontroller, an EPROM, a RAM, and customized ASIC which, together, control overall operation of the system 10. This control logic interfaces with a pair of transformers 188 mounted on the loader card 52. The microcontroller 186 further connects to a hook switch 190, a handset 179 and microphone 180 via an audio ringing code filter 192, two audio speakers 178 via a second audio ringing code filter 194, an analog/multiplex switch 195 and an audio amplifier 196. Volume control 198 enables an operator at the master station 32 to control volume of the speaker 178 with a microphone 180.

III. Operation

At startup, the operational software which actually controls the patient station 18 is dynamically downloaded from the master station 32. This allows software updates and modifications to be implemented without having to change a PROM in the patient stations 18. All patient stations 18 have a small program called the LOADER which is permanently stored in the 8K of program space on the 8752 microprocessor that serves as the CPU for each station. The main function of the LOADER program is to receive the downloaded operational software, which is stored in the 64K of RAM space of the patient station 18 as it is received. When the download is complete, the LOADER program first performs a checksum test to determine if the downloaded software is error-free, and if so, then switches the processors's program execution area to RAM, thereby beginning execution of the downloaded program. This allows for the running of a much larger program than could fit into the 8752's on-chip program area. Currently, the RAM executable program area is configured to be approximately 48K in size, with an additional 16K of RAM reserved for data space.

Three hardware/software components are involved in the download process (in addition to the PBX 60), as well as three data channels. The hardware/software components are the patient station 18, the loader card 52 and the master station PC 43. The data channels are the D-channel, the B-channel, and the RS-232 serial data link. The loader card 52 resides in the master station PC 43 and communicates therewith over the RS-232 link. It also communicates with the PBX 60. To the PBX 60, it looks like just another patient station 18. The binary image of the software to be downloaded to the patient station 18 is first transmitted to the loader card 52 over the serial data link. The loader card 52, upon receipt of the appropriate command from the master station PC 43, then transmits the binary image of the station software over the B-channel, which operates normally as the audio channel and which is much faster than the D-channel. The D-channel is used by all three components for synchronization and control. The loader card 52 communicates with the master station PC 43 over a serial data link. Actually, the loader card 52 looks like a serial adapter card to the master station PC 43 and is configured to communicate with the master station PC 43 over the MS-DOS COM4 channel at 19.2 k baud, with 8 data bits, no parity bits, and 1 stop bit.

When the application software for the system 10 boots up on the master station PC 43, it looks for a file called "SEND.BIN" in the default directory. This file is a binary image of the downloadable station software. It is transmitted to the loader card 52 in 256 byte blocks, plus a relatively small header block at the start. This transmission is essentially performed in the background, so that the system 10 can perform other functions at the same time. The downloading to the loader card 52 usually takes about 30 seconds.

When the loader card 52 receives the last block, it calculates an EXCLUSIVE-OR sum and a normal sum of a data received and compares the 2 sums with the 2 received checksums. If they match, it sends back an ASCII '0' followed by an ASCII 'OR' to the software of the master station 32. This constitutes an acknowledgement and the master station 32 considers the loader card 52 ready to download to the patient stations 18. The loader card 52 now has the binary image.

In the downloading process, the D-channel is used for synchronization and control, as well as for requests and responses. When a patient station 18 is first powered up, it performs a test to determine if it has downloaded software present (RAM is kept electrically charged for a few hours when there is no power to the station 18, so the station 18 software in RAM can be retained with no power) and performs a checksum test to determine if the software is valid. If so, the station 18 begins running the software in RAM. If it has no software in RAM or determines that the software is invalid, it begins sending 'download request' messages over the D-channel, to the master station 32. By default, these requests are sent once every 60 seconds. When the software at the master station 32 receives a request, if it is not currently waiting for a download to another station 18 to complete, it initiates the download process by sending a 'prepare for download' message to the station 18 and then sending a 'begin download' message to the loader card 52. It then opens a special voice channel between the station 18 and the loader card 52 to transmit the binary data from the loader card 52 to the patient station 18.

When the station 18 receives a 'prepare for download' message it sets a timer allowing about 15 seconds for completion of the downloading. If the station 18 receives the complete download, it resets the timer, and then performs a checksum test on the downloaded software which it now has sorted in RAM. If the test passes, the station 18 sends back a D-channel 'download successful response' message to the software of the master station 32, and the station 18 switches execution to the software in RAM. If the checksum test fails or if the station 18 timed out, it sends back a 'download response' message with an error code and subsequently resumes sending 'download request' messages until downloading succeeds.

The B-channel is normally used for audio communication in this system 10. Audio is converted to digital signals and then transformed by the PBX 60, resulting in a difference between the digital signal transmitted on the B-channel by one station 18 and the digital signal arriving at a destination station 18. In the downloading process, the B-channel is used to transmit a binary image from the loader card 52 to the station 18 being downloaded to, because data can be transmitted much faster over the B-channel than the D-channel. The B-channel can transmit 64000 bits per second, whereas the D-channel can effectively transmit only about 2000 bits per second.

However, to use the B-channel to transmit data, no PBX processing can be performed on the signal. So when an audio channel is opened between the loader card 52 and the patient station 18 to be downloaded to, the system 10 must essentially tell the DXP 60 to pass the digital audio signal through without processing it.

Also, when the station 18 receives the D-channel 'prepare for download' message, it sets itself up to temporarily route the incoming audio bits to a LOADER software download routine, instead of to the speaker, which is where audio is normally routed.

The protocol used for the transmission of the audio data from the loader card 52 to the patient station 18 is similar in some respects to the transmission of the data from the master station PC 43 to the loader card 52 over the serial channel. There is a header sent before the rest of the data and the actual binary image software data is transmitted 256 bytes at a time.

There the similarity ends. Part of the difference is due to the nature of the transmission medium. The serial channel is asynchronous, meaning that at any given moment, a serial byte may be in the process of being transmitted, but for long periods the serial channel may be idle. The audio channel, on the other hand, is synchronous, and is essentially never idle. This results in a higher possibility for error and loss of synchronization. Therefore, a special preamble is used to help insure that each patient station 18 recognizes the start of the header block, and another preamble is used for each 256 byte data block. Also, each data block has a checksum appended to it, which incorporates the loading address for that block. Finally, if the patient station 18 determines that the header block or a subsequent data block has errors in it because the block checksum test failed, it sends a "no acknowledgement" message to the loader card 52, and that block is retransmitted. A block may be retransmitted a maximum of six times before the process fails.

One of ordinary skill in the art will appreciate that the system to described can be programmably controlled to add or remove additional features to suit the needs of the particular hospital wing in which it is used. For instance, the "nurse follower" mode can be used by assigning one or more patients to a nurse on duty, storing the location of the nurse and then automatically indicating to the nurse, wherever he or she is located, that a call has been initiated by one of the assigned patients. This automatic indication may also include the initiation of a two-way audio link. As a variation of "nurse follower", emergency or highest priority calls may be forwarded to all nurses on duty.

Accompanying Appendices A and B (see Microfische Appendix) depict preferred operational interfaces for interacting with the system 10 at the master station 32 and at the patient stations 18, respectively. More specifically, Appendices A and B illustrate what appears on displays 34 and 118 at the master station 32 and the patient station 18, respectively, and how these displays change via selective rotation and depression of the control wheels 176 and 117.

The tables included at the end of this section are designated Table A-1 through Table A-110, and, in connection with the screens depicted in Appendix A, they show the control flow of operation from one screen to the next at the master station 32. Every screen identified in Appendix A corresponds to one of the following tables. Each screen in Appendix A is identified in its lower right hand corner by a two part identification. The first part indicates the section or tile highlighted on the screen, and the second part indicates the number of an option associated with that section of the screen. If the second part of the identification is a 0, the screen appears exactly as the display 34 appears prior to selection of that option i.e., initial depression of the control wheel 176. Additionally, some screen identifications have a third part, which is a lower case letter in parentheses. These screens represent a formatting variation on the original screen definition. This format variation is data dependent and in of itself does not affect flow control. The screen flows start out at the home screen, and progress through the seven main tiles, which are designated ANSWER, CALL, PAGE, LOCATE, INFO, SET-UP and LEARN.

A-1

| SCREEN | EVENT | NEW SCREEN |
|---|---|---|
| HOME-1 | New Waiting Call Received - Msg 1.1 | ANSWER-1 |
| | Select "Answer" - Call Exists | ANSWER-1 |
| | Select "Answer" - No Call Exists | ANSWER-11 |
| | Scroll to "Call" | CALL-0 |
| | Scroll to "Page" | PAGE-0 |
| | Scroll to "Locate" | LOCATE-0 |
| | Scroll to "Info" | INFO-0 |
| | Scroll to "Setup" | SETUP-0 |
| | Scroll to "Learn" | LEARN-0 |
| | Handset Pickup[1]<br>If there are Waiting Calls,<br>Answer Top Priority Waiting Call | ANSWER-2<br>ANSWER-16,<br>ANSWER-18,<br>ANSWER-21<br>(Depending on<br>type of call[2]) |

A-2

| SCREEN | EVENT | NEW SCREEN |
|---|---|---|
| ANSWER-1[3] | Call Selection: Patient Call | ANSWER-2 |
| | Call Selection: Staff Call | ANSWER-16 |
| | Call Selection: Equipment Call | ANSWER-20 |
| | Call Selection: Code Blue Call | ANSWER-18 |
| | List Termination (scroll out of vertical list) | ANSWER-12 |

| | | | |
|---|---|---|---|
| ANSWER-2 | Select "Hangup"; Latching Call | ANSWER-15 | A-3 |
| | Select "Hangup"; Non-Latching Call | ANSWER-14 | |
| | Select "Put on Hold" | ANSWER-4 | |
| | Select "Takeoff Hold" | ANSWER-3 | |
| | Select "Call" | ANSWER-5 | |
| | Select "Page" | PAGE-1 | |

| | | | |
|---|---|---|---|
| ANSWER-3 | See ANSWER-2 for branching details | | A-4 |

| | | | |
|---|---|---|---|
| ANSWER-4 | See ANSWER-2 for branching details | | A-5 |

| | | | |
|---|---|---|---|
| ANSWER-5 | Select "Patient's Nurse"; Nurse Assigned and Registered | ANSWER-6 | A-6 |
| | Select "Patient's Nurse"; Nurse not Assigned or not Registered | ANSWER-7 | |
| | Select "Nearest Nurse"; Nurse Found | ANSWER-8 | |
| | Select "Nearest Nurse"; Nurse not Found | ANSWER-22 | |
| | Select "Other Staff" | ANSWER-9 | |
| | Select "Location" | ANSWER-23 | |
| | Select "Return" | ANSWER-2, ANSWER-3, ANSWER-4, ANSWER-8, ANSWER-16, ANSWER-20, ANSWER-24, (Depending on how User got to ANSWER-5) | |

| | | | |
|---|---|---|---|
| ANSWER-6 | Select "Hangup"; Latching Call | ANSWER-15 | A-7 |
| | Select "Hangup"; Non-Latching Call | ANSWER-14 | |
| | Select "Connect to Staff" | ANSWER-10 | |
| | Select "Call" | ANSWER-5 | |
| | Select "Page" | PAGE-1 | |

| | | | |
|---|---|---|---|
| ANSWER-7 | Select "OK" | ANSWER-5 | A-8 |
| | Timeout - 30 sec Default | ANSWER-5 | |

| | | | |
|---|---|---|---|
| ANSWER-8 | See ANSWER-6 for branching details | | A-9 |

| | | | |
|---|---|---|---|
| ANSWER-9 | Nurse Selection; Nurse Registered | ANSWER-13 | A-10 |
| | Nurse Selection; Nurse Not Registered | ANSWER-17 | |
| | Select "Done" | ANSWER-5 | |

| | | | |
|---|---|---|---|
| ANSWER-10 | Select "OK" | HOME-1 | A-11 |
| | Timeout - 30 sec Default | HOME-1 | |

| | | | |
|---|---|---|---|
| ANSWER-11 | Select "OK" | HOME-1 | A-12 |
| | Timeout - 30 sec Default | HOME-1 | |

| | | | |
|---|---|---|---|
| ANSWER-12 | Stay in List | ANSWER-1 | A-13 |
| | Leave the List | HOME-1 | |

| | | | |
|---|---|---|---|
| ANSWER-13 | See ANSWER-6 for branching details | | A-14 |

| | | | |
|---|---|---|---|
| ANSWER-14 | Select "Yes" | HOME-1 | A-15 |
| | Select "No" | HOME-1 | |

| | | | |
|---|---|---|---|
| ANSWER-15 | Select "OK" | HOME-1 | A-16 |
| | Timeout - 30 sec Default | HOME-1 | |

| ANSWER-16 | Select "Hangup"; Latching Call | ANSWER-15 | A-17 |
| --- | --- | --- | --- |
| | Select "Hangup"; Non-Latching Call | ANSWER-14 | |
| | Select "Put on Hold" | ANSWER-16 | |
| | Select "Take off Hold" | ANSWER-16 | |
| | Select "Call" | ANSWER-5 | |
| | Select "Page" | PAGE-1 | |
| | Select "Info" | INFO-1 | |

| ANSWER-17 | Select "OK" | ANSWER-5 | A-18 |
| --- | --- | --- | --- |
| | Timeout - 30 sec Default | ANSWER-5 | |

| ANSWER-18 | Select "Hangup"; Latching Call | ANSWER-15 | A-19 |
| --- | --- | --- | --- |
| | Select "Hangup"; Non-Latching Call | ANSWER-14 | |
| | Select "Initiate CODE BLUE Response" | ANSWER-19 | |

| ANSWER-19 | Select "OK" | ANSWER-18 | A-20 |
| --- | --- | --- | --- |
| | Timeout - 30 sec Default | ANSWER-18 | |

| ANSWER-20 | Select "Acknowledge Call"; Latching Call | ANSWER-15 | A-21 |
| --- | --- | --- | --- |
| | Select "Acknowledge Call"; Non-Latching Call | ANSWER-14 | |
| | Select "Talk to Patient" | ANSWER-21 | |
| | Select "Call" | ANSWER-5 | |
| | Select "Page" | PAGE-1 | |

| ANSWER-21 | See ANSWER-2 for branching details | | A-22 |
| --- | --- | --- | --- |

| ANSWER-22 | Select "OK" | ANSWER-5 | A-23 |
| --- | --- | --- | --- |
| | Timeout - 30 sec Default | ANSWER-5 | |

| ANSWER-23 | Select Location | ANSWER-24 | A-24 |
| --- | --- | --- | --- |
| | Select "Done" | ANSWER-5 | |

| ANSWER-24 | See ANSWER-6 for branching details | | A-25 |
| --- | --- | --- | --- |

| SCREEN | EVENT | NEW SCREEN | A-26 |
| --- | --- | --- | --- |
| CALL-0[4] | Select "Call": | | |
| |    If Staff Locator is part of system | CALL-1 | |
| |    If Staff Locator is NOT part of system | CALL-4 | |
| | Scroll to "Answer" | AWNSER-0 | |
| | Scroll to "Page" | PAGE-0 | |

| CALL-1 | Select "Staff" | CALL-2 | A-27 |
| --- | --- | --- | --- |
| | Scroll to "Patient" | CALL-4 | |

| CALL-2 | Select Located Staff Member | CALL-3 | A-28 |
| --- | --- | --- | --- |
| | Select Non-Located Staff Member | CALL-12 | |
| | Select "Done" | CALL-0 | |

| CALL-3 | Select "Hangup" | CALL-0 | A-29 |
| --- | --- | --- | --- |
| | Select "Put on Hold" | CALL-3 | |
| | Select "Takeoff Hold" | CALL-3 | |
| | Select "Call" | CALL-1 | |
| | Select "Page" | PAGE-1 | |

| CALL-4 | Select "Patient" | CALL-5 | A-30 |
| --- | --- | --- | --- |
| | Scroll to "Location" | CALL-7 | |
| | If Staff Locator is part of system, Scroll to "Staff" | CALL-1 | |

| CALL-5 | Select Patient Name | CALL-6 | A-31 |
| --- | --- | --- | --- |
| | Select "Done" | CALL-0 | |

| | | | |
|---|---|---|---|
| CALL-6 | Select "Hangup" | CALL-0 | A-32 |
| | Select "Put on Hold" | CALL-6 | |
| | Select "Take Off Hold" | CALL-6 | |
| | Select "Call" | CALL-1 | |
| | Select "Page" | PAGE-1 | |

| | | | |
|---|---|---|---|
| CALL-7 | Select "Location" | CALL-8 | A-33 |
| | Scroll to "Patient" | CALL-4 | |
| | Scroll up: | | |
| |    If No Room Monitoring (select Return) | CALL-0 | |
| |    If Room Monitoring Active | CALL-10 | |

| | | | |
|---|---|---|---|
| CALL-8 | Select desired location | CALL-9 | A-34 |
| | Select Done | CALL-0 | |

| | | | |
|---|---|---|---|
| CALL-9 | Select "Hangup" | CALL-0 | A-35 |
| | Select "Put on Hold" | CALL-9 | |
| | Select "Take off Hold" | CALL-9 | |
| | Select "Call" | CALL-1 | |
| | Select "Page" | PAGE-1 | |

| | | | |
|---|---|---|---|
| CALL-10 | Select "Monitored Room" | CALL-11 | A-36 |
| | Scroll to "Location" | CALL-7 | |
| | Scroll to "Return"/Select | CALL-0 | |

| | | | |
|---|---|---|---|
| CALL-11 | Select "Hangup" | CALL-0 | A-37 |
| | Select "Put on Hold" | CALL-11 | |
| | Select "Take off Hold" | CALL-11 | |
| | Select "Call" | CALL-1 | |
| | Select "Page" | PAGE-1 | |

| | | | |
|---|---|---|---|
| CALL-12 | Select "OK" | CALL-2 | A-38 |
| | Timeout - 30 sec Default | CALL-0 | |

| | | | |
|---|---|---|---|
| PAGE-0[5] | Select "Page" | PAGE-1 | A-39 |
| | Scroll to "Call" | CALL-0 | |
| | If Locator in System, scroll to "Locator" | LOCATE-0 | |
| | If Locator NOT in System, scroll to "Locator" | INFO-0 | |

| | | | |
|---|---|---|---|
| PAGE-1 | Select "Rooms" | Page-2 | A-40 |
| | Select "Return" | PAGE-0 | |

| | | | |
|---|---|---|---|
| PAGE-2 | Select a Room | PAGE-3 | A-41 |
| | Select "Done" | PAGE-0 | |

| | | | |
|---|---|---|---|
| PAGE-3 | Pick up handset | PAGE-4 | A-42 |
| | Select "Cancel" | PAGE-2 | |

| | | | |
|---|---|---|---|
| PAGE-4 | Hangup handset | PAGE-0 | A-43 |
| | Select "Hangup" | PAGE-0 | |
| | No Hangup | PAGE-5 | |

| | | | |
|---|---|---|---|
| PAGE-5 | Select "OK" | PAGE-0 | A-44 |
| | Timeout - 30 sec Default | PAGE-0 | |

| | | | |
|---|---|---|---|
| LOCATE-0[6] | Select "Locate" | LOCATE-1 | A-45 |
| | Scroll to "Page" | PAGE-0 | |
| | Scroll to "Info" | INFO-0 | |

| | | | |
|---|---|---|---|
| LOCATE-1 | Select "Staff" | LOCATE-2 | A-46 |
| | Scroll to Return / Select | LOCATE-0 | |

| | | | |
|---|---|---|---|
| LOCATE-2 | Select Located Staff Member | LOCATE-3 | A-47 |
| | Select Non-Located Staff Member | LOCATE-4 | |
| | Select Done | LOCATE-0 | |

| | | | |
|---|---|---|---|
| LOCATE-3 | Select "Hangup" | LOCATE-0 | A-48 |
| | Select "Put on Hold" | LOCATE-3 | |
| | Select "Take off Hold" | LOCATE-3 | |
| | Select "Call" | CALL-1 | |
| | Select "Page" | PAGE-1 | |

| | | | |
|---|---|---|---|
| LOCATE-4 | Select "OK" | LOCATE-2 | A-49 |
| | Timeout - 30 sec Default | HOME-1 | |

| | | | |
|---|---|---|---|
| INFO-0[7] | Select "Info" | INFO-1 | A-50 |
| | Scroll to "Setup" | SETUP-0 | |
| | If Locator in System, scroll to "Locator" | LOCATE-0 | |
| | If Locator NOT in System, scroll to "PAGE" | PAGE-0 | |

| | | | |
|---|---|---|---|
| INFO-1 | Select Staff | INFO-STAFF-1 | A-51 |
| | Scroll to "Patient" | INFO-2 | |

| | | | |
|---|---|---|---|
| INFO-STAFF-1 | Select Done | INFO-0 | A-52 |
| | Select New Staff | INFO-STAFF-14 | |
| | Select Staff Member | INFO-STAFF-2 | |

| | | | |
|---|---|---|---|
| INFO-STAFF-2 | Select Done | INFO-0 | A-53 |
| | Scroll to "Select Another Staff" | INFO-STAFF-3 | |

| | | | |
|---|---|---|---|
| INFO-STAFF-3 | Select "Select Another Staff" | INFO-STAFF-1 | A-54 |
| | Scroll to "Next Staff" | INFO-STAFF-4 | |
| | Scroll to "Done" | INFO-STAFF-2 | |

| | | | |
|---|---|---|---|
| INFO-STAFF-4 | Select "Next Staff": | | A-55 |
| |   If there is a next Staff | INFO-STAFF-4 | |
| |   If no next Staff | INFO-STAFF-5 | |
| | Scroll to "Select Another Staff" | INFO-STAFF-3 | |
| | Scroll to "Previous Staff" | INFO-STAFF-6 | |

| | | | |
|---|---|---|---|
| INFO-STAFF-5 | Select "OK" | INFO-STAFF-4 | A-56 |

| | | | |
|---|---|---|---|
| INFO-STAFF-6 | Select "Previous Staff": | | A-57 |
| |   If there is previous Staff | INFO-STAFF-6 | |
| |   If no previous Staff | INFO-STAFF-7 | |
| | Scroll to "Next Staff" | INFO-STAFF-4 | |
| | Scroll to "Edit Staff" | INFO-STAFF-7 | |

| | | | |
|---|---|---|---|
| INFO-STAFF-7 | Select "OK" | INFO-STAFF-6 | A-58 |

| | | | |
|---|---|---|---|
| INFO-STAFF-8 | Select "Edit Staff | INFO-STAFF-9 | A-59 |
| | Scroll to "New Staff" | INFO-STAFF-13 | |
| | "Scroll to "Previous Staff" | INFO-STAFF-6 | |

| | | | |
|---|---|---|---|
| INFO-STAFF-9 | Select Done: | | A-60 |
| |   If changes were made | Info-Staff-12 | |
| |   If no changes were made | Info-Staff-18 | |
| | Select field for update | INFO-STAFF-10,11 | |

| SCREEN | EVENT | NEW SCREEN | |
|---|---|---|---|
| INFO-STAFF-10 | Example field edit | | A-61 |
| | Select field | INFO-STAFF-11 | |
| | Scroll to other fields | INFO-STAFF-9 | |

| | | | |
|---|---|---|---|
| INFO-STAFF-11 | Select "Title" | INFO-STAFF-10 | A-62 |
| | Scroll to title selections | INFO-STAFF-11 | |

| | | | |
|---|---|---|---|
| INFO-STAFF-12 | Select Yes | INFO-STAFF-7 | A-63 |
| | Select No | INFO-STAFF-7 | |

| | | | |
|---|---|---|---|
| INFO-STAFF-13 | Select "New Staff" | INFO-STAFF-14 | A-64 |
| | Scroll to "Delete Staff" | INFO-STAFF-16 | |
| | Scroll to "Edit Staff" | INFO-STAFF-7 | |

| | | | |
|---|---|---|---|
| INFO-STAFF-14 | Select Done: | | A-65 |
| |   If changes were made | INFO-STAFF-15 | |
| |   If no changes were made | INFO-STAFF-18 | |
| | Do data entry: | | |
| | See INFO-STAFF-9, 10, 11 for examples | | |

| | | | |
|---|---|---|---|
| INFO-STAFF-15 | Select Yes: | INFO-STAFF-13, or | A-66 |
| |   Return to where "New" was initiated | INFO-STAFF-1 | |
| | Select No | INFO-STAFF-13, or | |
| |   Return to where "New" was initiated | INFO-STAFF-1 | |

| | | | |
|---|---|---|---|
| INFO-STAFF-16 | Scroll to "New Staff" | INFO-STAFF-13 | A-67 |
| | Select "Delete Staff" | INFO-STAFF-17 | |

| | | | |
|---|---|---|---|
| INFO-STAFF-17 | Select Yes | INFO-STAFF-16 | A-68 |
| | Select No | INFO-STAFF-16 | |

| | | | |
|---|---|---|---|
| INFO-STAFF-18 | Select "OK" | | A-69 |
| |   If we came from INFO-STAFF-9 | INFO-STAFF-7 | |
| |   If we came from INFO-STAFF-14 | INFO-STAFF-13 | |

| SCREEN | EVENT | NEW SCREEN | |
|---|---|---|---|
| INFO-2 | Select Patient | INFO-PAT-1 | A-70 |
| | Scroll Down | INFO-1 | |
| | Scroll up | INFO-ASSG-1 | |

| | | | |
|---|---|---|---|
| INFO-PAT-1 | Select Done | INFO-0 | A-71 |
| | Select New | INFO-PAT-5 (cleared) | |
| | Select a Patient | INFO-PAT-2 | |

| | | | |
|---|---|---|---|
| INFO-PAT-2 | Select Done | INFO-0 | A-72 |
| | Scroll to "Select Another Patient" | See Note | |

| | | | |
|---|---|---|---|
| INFO-PAT-3 | Scroll to "Select Another Patient" | See Note | A-73 |
| | Scroll to "Previous Staff" | See Note | |
| | Select "Next Patient": | | |
| |   If there is a next patient | INFO-PAT-3 | |
| |   If no next patient | See Note | |

| | | | |
|---|---|---|---|
| INFO-PAT-4 | Select "Edit patient" | See Note | A-74 |
| | Scroll to "Previous Patient" | See Note | |
| | Scroll to "New Patient" | INFO-PAT-5 (cleared) | |

| | | | |
|---|---|---|---|
| INFO-PAT-5 | Exmple of Title Selection Pop-Up | — | A-75 |

| INFO-PAT-6 | Example of field edit; | | A-76 |
| --- | --- | --- | --- |
| | Select Room & Bed | INFO-PAT-7 | |
| | Scroll to another field | See other field examples | |

| INFO-PAT-7 & INFO-PAT-8 | Example of Room & Bed Selection Pop-Up: | | A-77 |
| --- | --- | --- | --- |
| | Scroll to another Room | INFO-PAT-7 | |
| | Select Room & Bed: | | |
| |   If occupied | INFO-PAT-9 | |
| |   If NOT occupied | INFO-PAT-6 | |

| INFO-PAT-9 | Select SWAP | INFO-PAT-6 | A-78 |
| --- | --- | --- | --- |
| | Select CANCEL | INFO-PAT-7 | |

| INFO-PAT-10 | Example of Priority Selection Pop-Up | — | A-79 |
| --- | --- | --- | --- |

| INFO-PAT-11 | Example of Notes Selection Pop-Up | — | A-80 |
| --- | --- | --- | --- |

| INFO-PAT-12 | Select "New Patient" | INFO-PAT-5 | A-81 |
| --- | --- | --- | --- |
| | Scroll to "Delete Patient" | INFO-PAT-13 | |
| | Scroll to "Edit Patient" | INFO-PAT-4 | |

| INFO-PAT-13 | Scroll "New Patient" | INFO-PAT-12 | A-82 |
| --- | --- | --- | --- |
| | Select "Delete Patient" | See Note | |

| INFO-ASSG-1 | Select "Assignments" | INFO-ASSG-2 | A-83 |
| --- | --- | --- | --- |
| | Scroll up to "Reminder" | INFO-REM-1 | |
| | Scroll down tp "Patients" | INFO-PAT-1 | |

| INFO-ASSG-2 | Select "Done" | INFO-0 | A-84 |
| --- | --- | --- | --- |
| | Select "Change Assignments" | INFO-ASSG-3 | |

| INFO-ASSG-3 | Select "Change Assignments" | INFO-ASSG-4 | A-85 |
| --- | --- | --- | --- |
| | Scroll to "List B Patient" | INFO-ASSG-6 | |
| | Scroll to "Done" | INFO-ASSG-2 | |

| INFO-ASSG-4 | Select "Done" | INFO-ASSG-3 | A-86 |
| --- | --- | --- | --- |
| | Select Staff Members | INFO-ASSG-5 | |

| INFO-ASSG-5 | Select/Deselect Patient | INFO-ASSG-5 | A-87 |
| --- | --- | --- | --- |
| | Select Done | INFO-ASSG-4 | |

| INFO-ASSG-6 | Select "List by Patient" | INFO-ASSG-12 | A-88 |
| --- | --- | --- | --- |
| | Scroll up to "Change Assignments" | INFO-ASSG-3 | |
| | Scroll to "View Staff Info" | INFO-ASSG-7 | |

| INFO-ASSG-7 | Select "View Staff Info" | INFO-ASSG-8 | A-89 |
| --- | --- | --- | --- |
| | Scroll to "List by Patient" | INFO-ASSG-6 | |
| | Scroll to "Browse List" | INFO-ASSG-10 | |

| INFO-ASSG-8 | Select Staff Name | INFO-ASSG-9 | A-90 |
| --- | --- | --- | --- |
| | Select "Done" | INFO-ASSG-3 | |

| INFO-ASSG-9 | Select "Done" | INFO-ASSG-8 | A-91 |
| --- | --- | --- | --- |

| INFO-ASSG-10 | Select "Browse List" | INFO-ASSG-11 | A-92 |
| --- | --- | --- | --- |
| | Scroll to "View Staff Info" | INFO-ASSG-7 | |

| INFO-ASSG-11 | Scroll List | INFO-ASSG-11 | A-93 |
| | Select a name | INFO-ASSG-3 | |
| | Select "Done" | INFO-ASSG-3 | |

| INFO-ASSG-12 | Select "Change Assignments" | INFO-ASSG-13 | A-93 |
| | Scroll to "Done" | INFO-ASSG-2 | |
| | Scroll to "List by Staff" | INFO-ASSG-15 | |

| INFO-ASSG-13 | Select Patient Name | INFO-ASSG-14 | A-94 |
| | Select "Done" | INFO-ASSG-12 | |

| INFO-ASSG-14 | Select Staff Name | INFO-ASSG-14 | A-95 |
| | Select "Done" | INFO-ASSG-13 | |

| INFO-ASSG-15 | Select "List by Staff" | INFO-ASSG-3 | A-96 |
| | Scroll to "Change Assignments" | INFO-ASSG-12 | |
| | Scroll to "View Staff Info" | INFO-ASSG-16 | |

| INFO-ASSG-16 | Select "View Patient Info" | INFO-ASSG-17 | A-97 |
| | Scroll to "List by Staff" | INFO-ASSG-15 | |
| | Scroll to "Browse List" | INFO-ASSG-19 | |

| INFO-ASSG-17 | Select Patient Name | INFO-ASSG-18 | A-98 |
| | Select "Done" | INFO-ASSG-12 | |

| INFO-ASSG-18 | Select "Done" | INFO-ASSG-17 | A-99 |

| INFO-ASSG-19 | Select "Browse List" | INFO-ASSG-20 | A-100 |
| | Scroll to "View Patient Data" | INFO-ASSG-16 | |

| INFO-ASSG-20 | Select "Done" | INFO-0 | A-101 |

| SCREEN | EVENT | NEW SCREEN | A-102 |
| SETUP-0 | Select "Setup" | SETUP-MS-1 | |

| SETUP-MS-1 | Select "Master Station" | SETUP-MS-2 | A-103 |
| | Scroll to "Call Forwarding" | SETUP-CF-1 | |

| SETUP-MS-2 | Select "Done" | SETUP-0 | A-104 |

| SETUP-CF-1 | Select "Call Forwarding" | SETUP-CF-2 | A-105 |
| | Scroll Up to "Monitor" | SETUP-MON-1 | |
| | Scroll Down to "Master Station" | SETUP-MS-1 | |

| SETUP-CF-2 | Select Staff Name | SETUP-CF-3 | A-106 |
| | Select "Done" | SETUP-0 | |

| SETUP-CF-3 | Select Patient Name | SETUP-CF-3 | A-107 |
| | Select "Set all patients to Yes" | SETUP-CF-3 | |
| | Select "Set all patients to No" | SETUP-CF-3 | |
| | Select "Done" | SETUP-CF-2 | |

| SETUP-MON-1 | Select "Monitor" | SETUP-MON-2 | A-108 |
| | Scroll up to "System" | SETUP-SYS-1 | |
| | Scroll down to "Call Forwarding" | SETUP-CF-1 | |

| | | | |
|---|---|---|---|
| SETUP-MON-2 | Select Monitoring Room | SETUP-MON-2 | A-109 |
| | Select "Done" | SETUP-0 | |

| | | | |
|---|---|---|---|
| SETUP-SYS-1 | This goes into a "System" world which will be defined at some later time | | A-110 |

Appendix B is a flow chart which schematically depicts screen displays in operating the control wheel 117 at patient station 18.

While a preferred embodiment of a patient/nurse call system 10 in accordance with this invention has been described, it is to be understood that the functional and operational capabilities of the system 10 can be varied widely to suit the particular needs of a hospital in which it is used, or even a facility other than a hospital, wherein similar communication capabilities are desired. For instance, the particular coding and prioritizing of hospital calls may be varied, along with storage and retrieval of the calls and nurse location and identification information. Moreover, the manner of interfacing with the stored information at either the master station 32 or any of the patient stations 18 may also be modified, all without departing from the spirit and the scope of the invention as claimed hereafter.

We claim:

1. A patient/nurse call system for a hospital comprising:

a plurality of transmitters, each transmitter adapted to periodically transmit a pulse-coded infrared signal;

a plurality of patient stations, each patient station being located in a patient room in the hospital and including a receiver to receive and validate a pulse-coded infrared signal from any of the transmitters and generate a corresponding transmitter identification signal;

a signal processor operatively connected to the patient stations to receive each of the transmitter identification signals and generate a signal pair comprising the transmitter identification signal and a respective location identification signal, the location identification signal being representative of the location of the patient station which received the transmitter identification signal;

a master station operatively connected to the signal processor and adapted to receive and store the signal pairs in a memory; and each patient station further including a control to initiate a retrieval of the stored signal pairs from the master station, thereby disseminating transmitter identity and location identity information to any patient station upon a request from said any patient station.

2. The system of claim 1 wherein the transmitters comprise battery powered badges worn by nurses to be identified and located, and each transmitter identification signal corresponds to an identity of a nurse.

3. The system of claim 2 wherein each patient station further comprises;

a housing; and a display mounted to the housing, the display operatively connected to the control and adapted to visually display the retrieved signal pairs, whereby an operator at any patient station can visually display and thereby identify the locations of all nurses wearing the badges.

4. The system of claim 1 wherein the control includes a selector and retrieves stored signal pairs in response to an operator selecting a reference to the patient stations.

5. The system of claim 2 wherein the control includes a selector and retrieves stored signal pairs in response to an operator selecting a reference to the nurses.

6. The system of claim 3 wherein the control further comprises a rotatable and depressible control wheel mounted to the housing adjacent the display, the control wheel being rotated to designate one of a plurality of functions shown on the display and depressible to select the one of the functions.

7. The system of claim 1 wherein each transmitter is adapted to transmit a data packet which comprises a first data string of binary data bits followed by a second data string of the same binary bits, the data bits in the second string inverted with respect to the data bits in the first string.

8. The system of claim 7 wherein the data packet further comprises at least one start bit transmitted prior to transmittal of the first and second data strings.

9. The system of claim 7 wherein the data packet has a duration of about 10 milliseconds.

10. The system of claim 9 wherein the data packet is transmitted about every 6 seconds.

11. The system of claim 2 wherein each of the transmitter badges further comprises:

means for indicating low battery power.

12. The system of claim 1 wherein each patient station further comprises:

indicating means operatively connected to the respective receiver for indicating receipt of a transmitted pulse-coded infrared signal.

13. The system of claim 10 wherein each patient station further comprises:

a hospital bed monitoring unit connected to a hospital bed in the respective hospital room, the monitoring unit adapted to sense at least one bed condition and to generate a bed condition signal in response thereto; and input means for operatively connecting the bed monitoring unit to the system at the respective patient station, thereby to relay to the memory of the master station the bed condition signals associated with the respective sensed bed conditions so that an operator at the master station may retrieve and display the bed condition signals from memory.

14. The system of claim 13 wherein one of the sensed bed conditions is incontinence.

15. The system of claim 13 wherein each bed has a unique serial number assigned thereto, and the master station stores the bed condition signals and the serial numbers of the beds.

16. The system of claim 2 further comprising:

a plurality of hall stations, each hall station operatively connected to a patient station and located in a hall of the hospital outside a respective patient room of the patient station;

a nurse call device in the respective patient room for generating a PATIENT call from the patient station to the master station; and means for providing an indication at a hall station of the existence of the PATIENT call.

17. The system of claim 16 and further comprising means for cancelling the PATIENT call from patient station and the indication thereof at the respective hall station upon receipt of a pulse-coded infrared signal from a badge worn by a nurse sensed in the respective patient room by a receiver associated with the patient station.

18. A patient/nurse call system for a hospital wing having a plurality of patient rooms comprising:

a master station with memory for storing data;

a patient station located in each of the patient rooms, the patient station being operatively connected to the master station and a plurality of devices for generating different hospital calls;

the patient station adapted to relay each of the hospital calls to the master station for storage in the memory; and each patient station further including a control to initiate retrieval of the hospital calls from said memory to the patient station, thereby disseminating hospital calls in the hospital wing to each of the patient stations in the patient rooms upon a request from said any patient station.

19. The call system of claim 18 wherein the master station classifies and stores for subsequent retrieval the hospital calls according to priority types and when the calls were received.

20. The patient/nurse call system of claim 18 wherein there is one patient station per patient bed in the patient rooms of the hospital wing.

21. The patient/nurse call system of claim 20 and further comprising:

a plurality of hall units, each hall unit associated with one of the patient rooms of the hospital wing and mounted in a hallway of the hospital wing adjacent a doorway of a respective patient room, the hall unit operatively connected to the patient station located in said respective patient room; and each hall unit further including means for indicating that a hospital call was generated for the respective patient room.

22. The nurse/call system of claim 21 wherein, for patient rooms with more than one patient bed, the indicating means of the hall unit identifies which of the two patient stations generated the hospital call.

23. The nurse/call system of claim 18 and further comprising:

an audio network interconnecting the patient stations and the master station, each station including selector controls for initiating an audio interconnection with any other station, thereby to enhance the capability of responding to calls generated from any other station of the system.

24. The nurse/call system of claim 23 wherein the audio network accommodates a plurality of two way, simultaneous audio interconnections between a plurality of pairs of patient stations.

25. The nurse/call system of claim 18 and further comprising:

a plurality of transmitting badges, each badge adapted to be worn by a nurse and to transmit a unique pulse-coded infrared signal;

the patient station further including a receiver adapted to receive an infrared signal from any of the badges and in response, to generate a corresponding identification signal;

a signal processor connected to the patient station to form a signal pair comprised of the identification signal and a location signal corresponding to the location of the patient station and to convey the signal pair to the memory of the master station; and a display connected to the control at each patient station to display the hospital calls and the identities and the locations of the badge-wearing nurses in the hospital wing, thereby to disseminate hospital calls and nurse identity and location information to the patient stations.

26. The nurse/call system of claim 25 further comprising:

a plurality of hall units, each hall unit associated with a patient room of the hospital wing and mounted in a hallway of the hospital wing adjacent a doorway of said respective patient room, the hall unit operatively connected to each patient station located in the respective patient room; and each hall unit further including, a first indicator being actuated in response to a PATIENT call generated from within the patient room, and a second indicator being actuated in response to the patient station receiving an infrared signal from a nurseworn badge indicating the presence of a nurse in the room.

27. The nurse/call system of claim 26 wherein the hall unit automatically cancels actuation of the first indicator in response to actuation of the second indicator.

28. The patient/nurse call system of claim 25 wherein the control and display at each of the patient stations displays the generated hospital calls in an order of priority established at the master station.

29. The patient/nurse call system of claim 18 wherein the plurality of devices comprises a PATIENT call initiating means further having a housing connected by hardwire to an outlet, the outlet operatively connected to the respective patient station, the housing having a depressible pushbutton which, when depressed, initiates a PATIENT call.

30. The patient/nurse call system of claim 29 further comprising:

an input jack at the end of the hardwire and connectable to the outlet;

means for generating a PATIENT EQUIPMENT call when the input jack is pulled from the outlet; and a disconnect switch operatively connected to the hardware adjacent the jack to selectively disable the generating means, thereby to enable the jack to be pulled from the outlet without generating the PATIENT EQUIPMENT call.

31. The patient/nurse call system of claim 18 wherein one of the call initiation means further comprises:

a pull bar mounted to the patient station, the pull bar movable to generate a CODE BLUE call.

32. The patient/nurse call system of claim 18 and further comprising:

each patient station being operatively connected to an outlet located adjacent a patient bed;

a bed status unit mounted to the patient bed and adapted to detect at least one bed condition and to generate a bed status signal in response thereto; and an electrical connector interconnecting the bed status unit and the outlet to convey said at least one bed status signal from the bed status unit to the patient station, the patient station adapted to convey the bed status signal to the master station.

33. The patient/nurse call system of claim 32 and further comprising:

a disconnect switch on the electrical connector, the switch having a first position for normal operation whereby inadvertent pulling of the connector from the outlet generates a PATIENT EQUIPMENT call and a second position whereby pulling the connector from the outlet does not generate the PATIENT EQUIPMENT call, the switch being selectively movable between the first and second positions.

34. The patient/nurse call system of claim 32 and further comprising:

an incontinence detector operatively connected to the bed status unit and adapted to detect patient incontinence and to generate an incontinence bed signal in response thereto, the bed status unit adapted to convey the incontinent signal to the master station.

35. The patient/nurse call system of claim 32 wherein each bed has a unique serial number assigned thereto, and the master station stores the bed condition signals and the serial numbers of the beds.

* * * * *